(12) United States Patent
Forrest et al.

(10) Patent No.: US 12,133,463 B2
(45) Date of Patent: Oct. 29, 2024

(54) ASYMMETRIC NON-FULLERENE ACCEPTOR AND ORGANIC PHOTOVOLTAIC DEVICE COMPRISING THE SAME

(71) Applicant: The Regents of the University of Michigan, Ann Arbor, MI (US)

(72) Inventors: Stephen R. Forrest, Ann Arbor, MI (US); Yongxi Li, Ann Arbor, MI (US)

(73) Assignee: The Regents of the University of Michigan

( * ) Notice: Subject to any disclaimer, the term of this patent is extended or adjusted under 35 U.S.C. 154(b) by 491 days.

(21) Appl. No.: 16/903,874

(22) Filed: Jun. 17, 2020

(65) Prior Publication Data
US 2021/0288267 A1  Sep. 16, 2021

Related U.S. Application Data

(60) Provisional application No. 62/875,035, filed on Jul. 17, 2019.

(51) Int. Cl.
| | |
|---|---|
| *H10K 85/60* | (2023.01) |
| *C07D 495/22* | (2006.01) |
| *C07D 495/04* | (2006.01) |
| *C07D 495/14* | (2006.01) |
| *H10K 30/00* | (2023.01) |
| *H10K 30/30* | (2023.01) |
| *H10K 30/50* | (2023.01) |

(52) U.S. Cl.
CPC ....... *H10K 85/6576* (2023.02); *C07D 495/22* (2013.01); *H10K 85/626* (2023.02); *C07D 495/04* (2013.01); *C07D 495/14* (2013.01); *H10K 30/00* (2023.02); *H10K 30/30* (2023.02); *H10K 30/50* (2023.02); *H10K 85/615* (2023.02); *H10K 85/621* (2023.02); *Y02E 10/549* (2013.01)

(58) Field of Classification Search
CPC . H01L 51/0074; H01L 51/0058; H01L 51/42; H01L 51/4253; C07D 495/22; C07D 495/04; C07D 495/14; Y02E 10/549; H10K 85/6576; H10K 85/626; H10K 30/00; H10K 30/30; H10K 30/50; H10K 85/615; H10K 85/621
See application file for complete search history.

(56) References Cited

FOREIGN PATENT DOCUMENTS

| WO | 2019090229 | 5/2019 | |
|---|---|---|---|
| WO | WO-2020062254 A1 * | 4/2020 | ....... A61F 13/15577 |

OTHER PUBLICATIONS

Yongxi Li "High Efficiency Near-Infrared and Semitransparent Non-Fullerene Acceptor Organic Photovoltaic Cells" J. Am. Chem. Soc. 2017, 139, 17114-17119 (Year: 2017).*
Yongxi Li "A near-infrared non-fullerene electron acceptor for high performance polymer solar cells" Energy Environ. Sci., 2017, 10, 1610 (Year: 2017).*
Bowei Gao, "Multi-component non-fullerene acceptors with tunable bandgap structures for efficient organic solar cells" J. Mater. Chem. A, 2018, 6, 23644 (Year: 2018).*

* cited by examiner

*Primary Examiner* — Michael Y Sun
(74) *Attorney, Agent, or Firm* — Riverside Law LLP

(57) ABSTRACT

The present invention relates in part to an asymmetric non-fullerene acceptor compound for use in organic photovoltaic (OPV) devices. The invention also relates in part to an OPV device comprising an asymmetric non-fullerene acceptor compound.

19 Claims, 10 Drawing Sheets

200 Multi-junction/Tandem Organic Photovoltaic Cell

| |
|---|
| 202 Anode |
| 208 Intermediate Layer |
| 206A Active Region/Layer |
| 212 Intermediate Layer |
| 206B Active Region/Laer |
| 210 Intermediate Layer |
| 204 Cathode |

| Blend | Condition | $q$ (nm$^{-1}$) | Long Period (nm) | ISI |
|---|---|---|---|---|
| PCE10:BT-IC | fresh | 0.16/0.35 | 39/18 | 0.93 |
| PCE10:BT-IC | aged | 0.12/0.33 | 52/19 | 1.00 |
| PCE10:BT-ClC-IC | fresh | 0.20 | 31 | 0.82 |
| PCE10:BT-ClC-IC | aged | 0.21 | 30 | 0.74 |
| PCE10:BT-ClC | fresh | 0.10 | 62 | 0.69 |
| PCE10:BT-ClC | aged | 0.10 | 62 | 0.70 |

ASYMMETRIC NON-FULLERENE ACCEPTOR AND ORGANIC PHOTOVOLTAIC DEVICE COMPRISING THE SAME

CROSS-REFERENCE TO RELATED APPLICATIONS

The present application claims priority to U.S. Provisional Patent Application Ser. No. 62/875,035, filed Jul. 17, 2019, the entire contents of which is incorporated herein by reference.

STATEMENT REGARDING FEDERALLY SPONSORED RESEARCH OR DEVELOPMENT

This invention was made with government support under Grant Number DE-EE0008561, awarded from the Department of Energy and Grant Number N00014-17-1-2211, awarded from the Office of Naval Research. The government has certain rights in the invention.

BACKGROUND OF THE INVENTION

Recent progress on developing n-type conjugated small molecules has led to significant advances in fullerene-free organic photovoltaics (OPVs). The power conversion efficiencies of OPVs were enhanced to about 15% by utilizing these new acceptor materials. In particular, these non-fullerene acceptors based solar cells show decreased energy loss, which sets the fundamental limits of open circuit voltage and hence the efficiency of OPVs. While this loss can be as large as 0.7 eV using fullerene acceptors, non-fullerene acceptors show promise for reducing this to ≤0.6 eV.

There is a need in the art for non-fullerene acceptors. The present invention satisfies this unmet need.

SUMMARY OF THE INVENTION

In one aspect, the present invention relates to a compound of formula (1) or a stereoisomer thereof

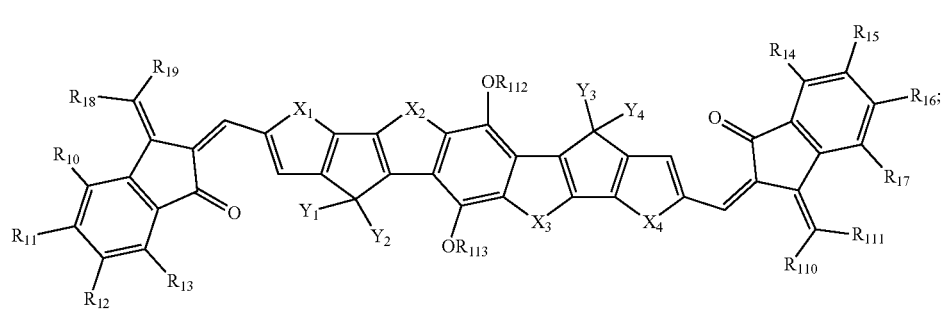

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$-alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof; $R_{18}$, $R_{19}$, $R_{110}$, and $R_{111}$ are each independently an electron withdrawing group selected from the group consisting of: halogen, C(=O)$R_{116}$, $SO_3R_{117}$, cyano, nitro, C($R_{118}$)$_3$, and combinations thereof; $R_{114}$-$R_{117}$ are each independently selected from the group consisting of hydrogen and $C_1$-$C_{20}$ alkyl; $R_{118}$ is a halogen selected from the group consisting of F, Cl, Br, and I; $R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl; $X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof. In one embodiment, each of $X_1$-$X_4$ are S. In one embodiment, $R_{10}$-$R_{13}$, $R_{14}$, and $R_{17}$ are each hydrogen; and $R_{15}$ and $R_{16}$ are each independently a halogen selected from the group consisting of: F, Cl, Br, and I. In one embodiment, $R_{10}$-$R_{13}$, $R_{14}$, and $R_{17}$ are each hydrogen; and $R_{15}$ and $R_{16}$ are each Cl. In one embodiment, $R_{18}$, $R_{19}$, $R_{110}$, and $R_{111}$ are each cyano. In one embodiment, $Y_1$-$Y_4$ are each independently selected from the group consisting of:

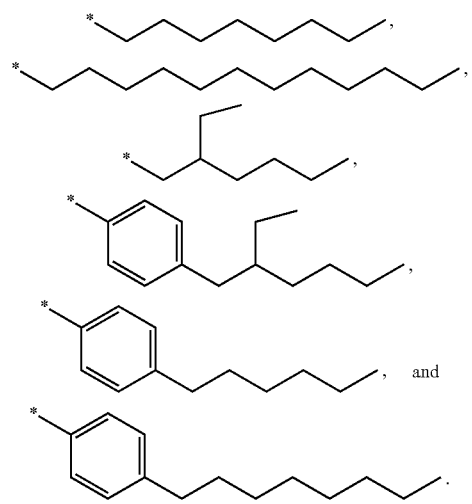

In one embodiment, $Y_1$-$Y_4$ are each

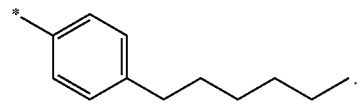

In one embodiment, $R_{112}$ and $R_{113}$ are each independently selected from the group consisting of:
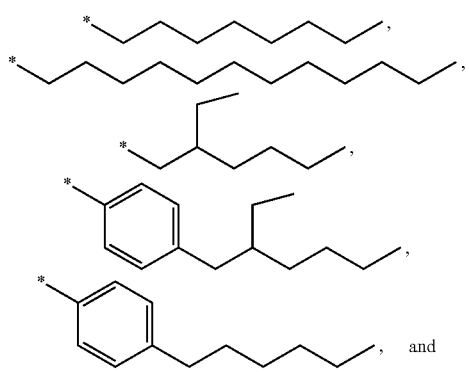
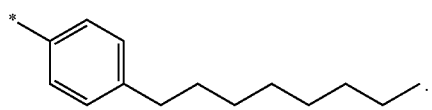
In one embodiment, the compound of formula (1) is selected from the group from the group consisting of:
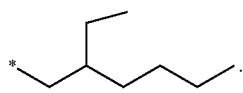
In one embodiment, $R_{112}$ and $R_{113}$ are each independently consisting of:
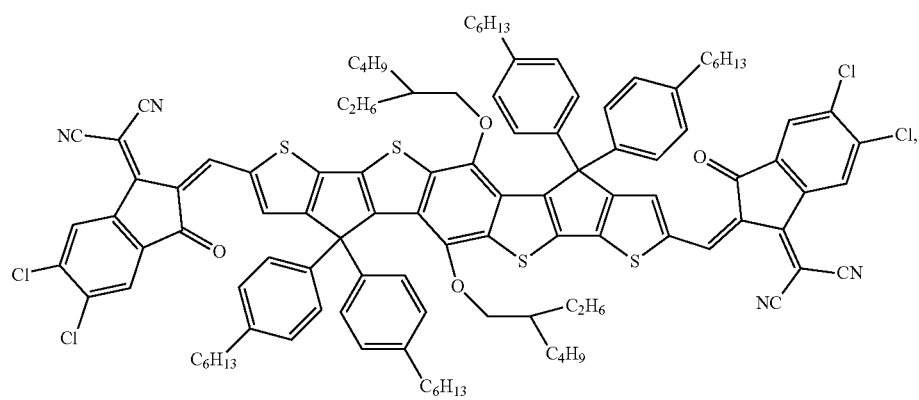
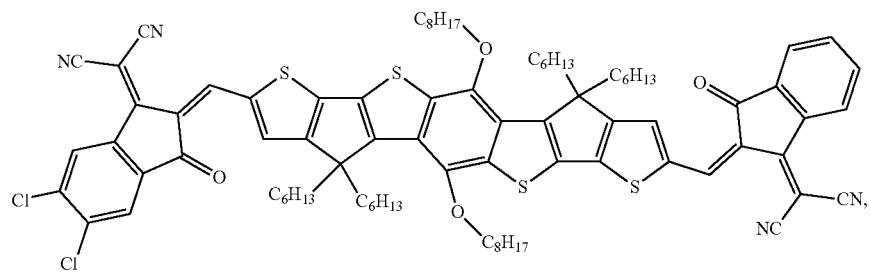
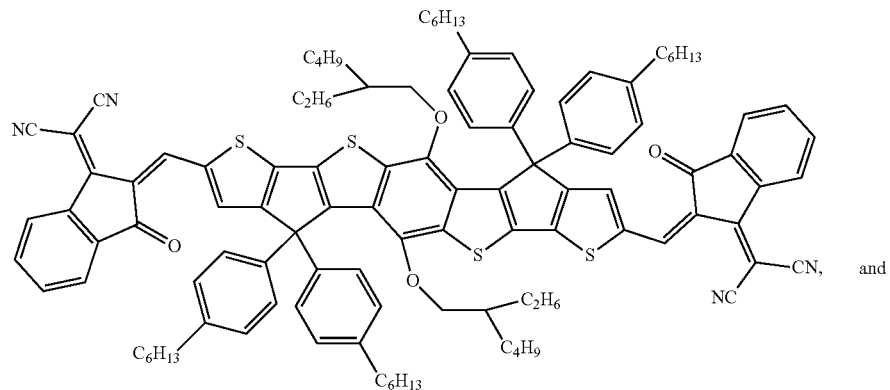

-continued

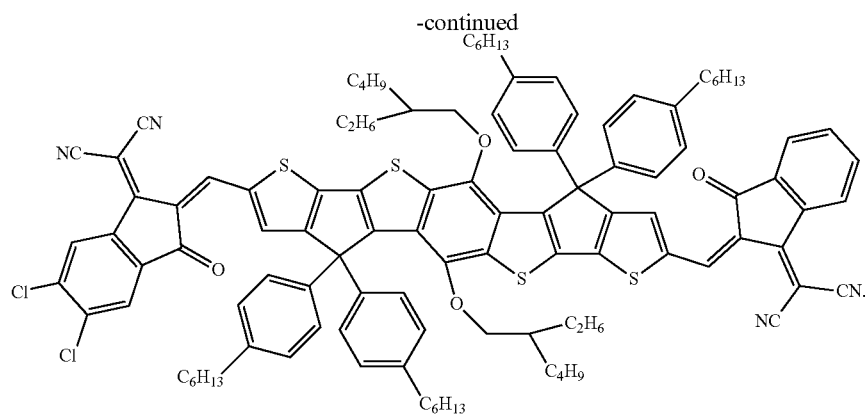

In another aspect, the present invention relates to an organic photovoltaic device comprising: an anode, a cathode, and an active layer between the anode and the cathode, wherein the active layer comprises a compound of formula (1) or a stereoisomer thereof:

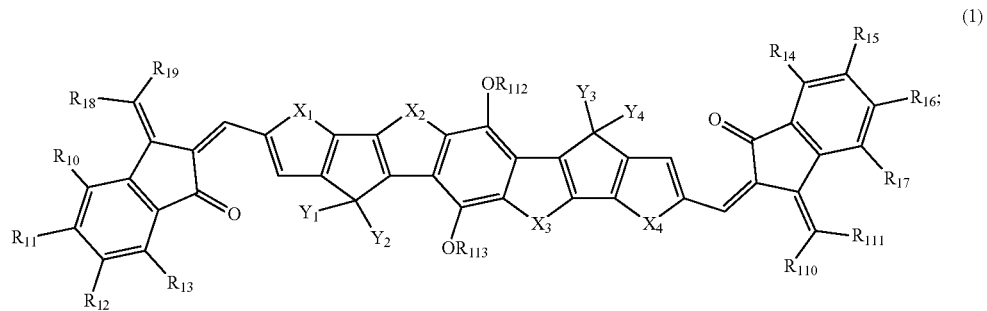

(1)

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$ alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof; $R_{18}$, $R_{19}$, $R_{110}$, and $R_{111}$ are each independently an electron withdrawing group selected from the group consisting of: halogen, $C(=O)R_{116}$, $SO_3R_{117}$, cyano, nitro, $C(R_{118})_3$, and combinations thereof; $R_{114}$-$R_{117}$ are each independently selected from the group consisting of hydrogen and $C_1$-$C_{20}$ alkyl; $R_{118}$ is a halogen selected from the group consisting of F, Cl, Br, and I; $R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl; $X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof. In one embodiment, the active layer further comprises a polymer selected from the group consisting of:

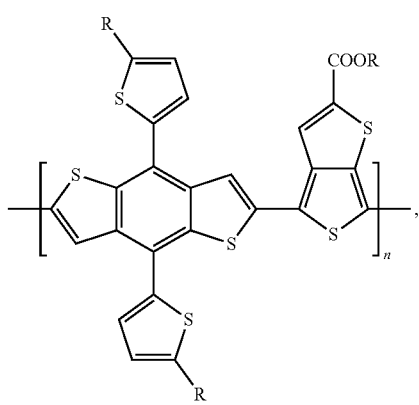
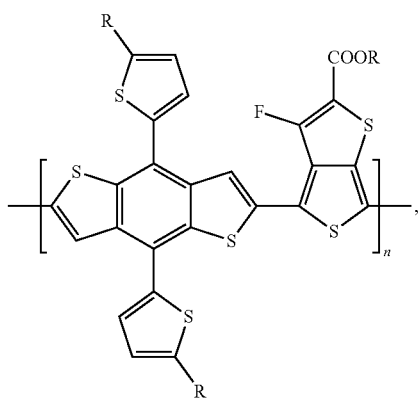
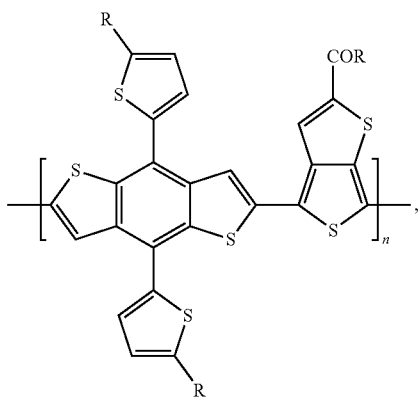
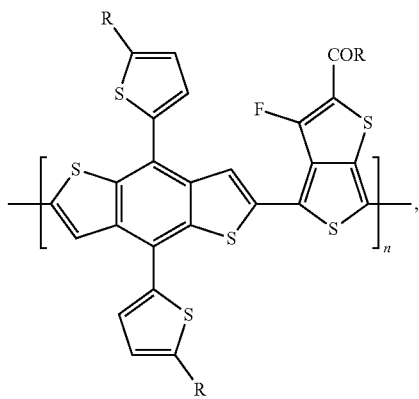
-continued
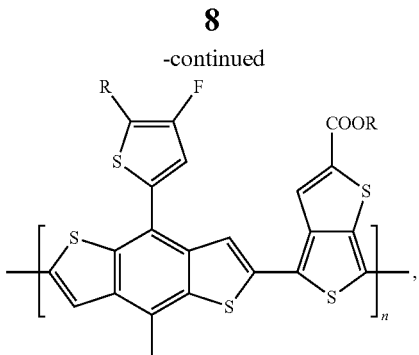
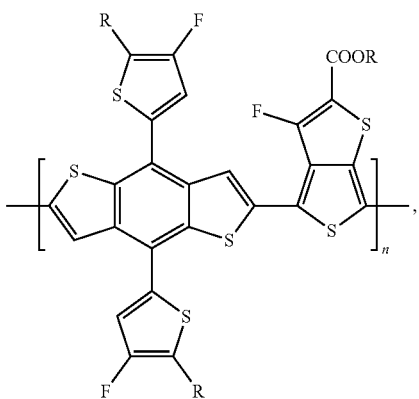
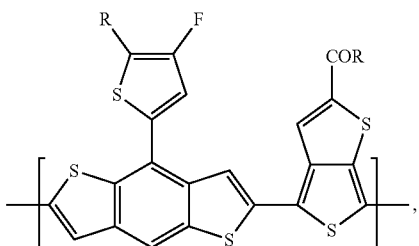
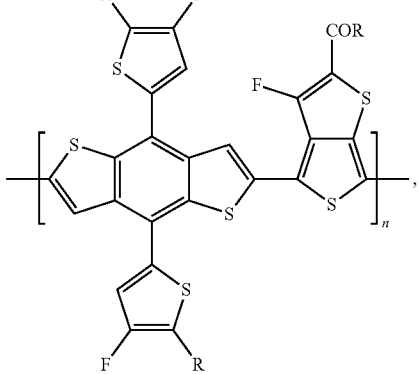

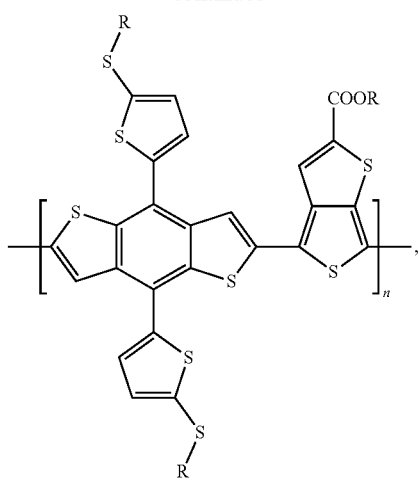
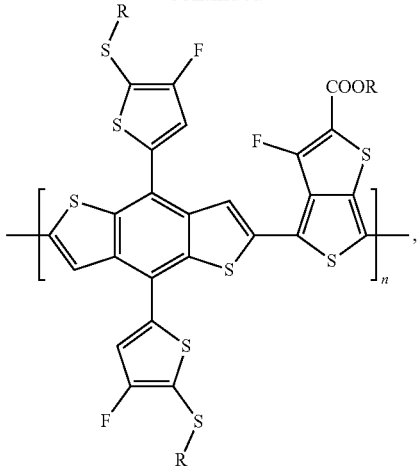
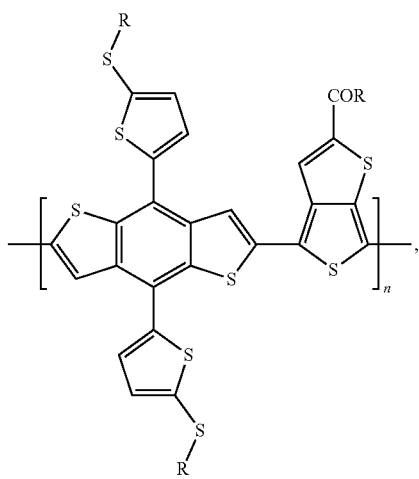
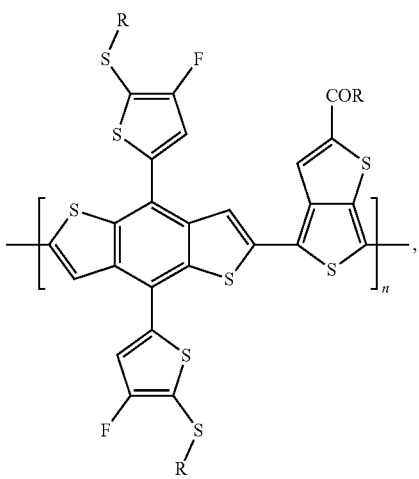
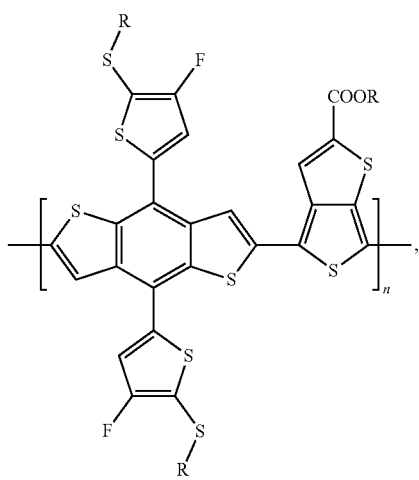
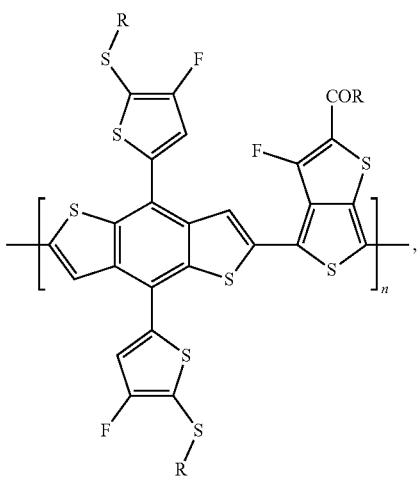

and derivatives thereof; wherein each R is independently a $C_1$-$C_{20}$ alkyl; and n is the degree of polymerization. In one embodiment, the polymer comprises
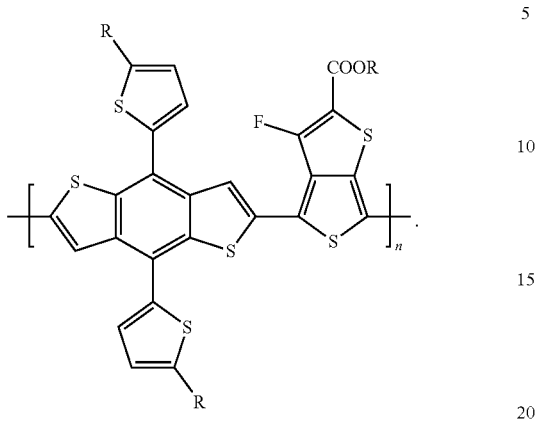
(5)
In one embodiment, each R represents 2-ethylhexyl. In one embodiment, the acceptor represented by formula (1) is selected from the group consisting of:
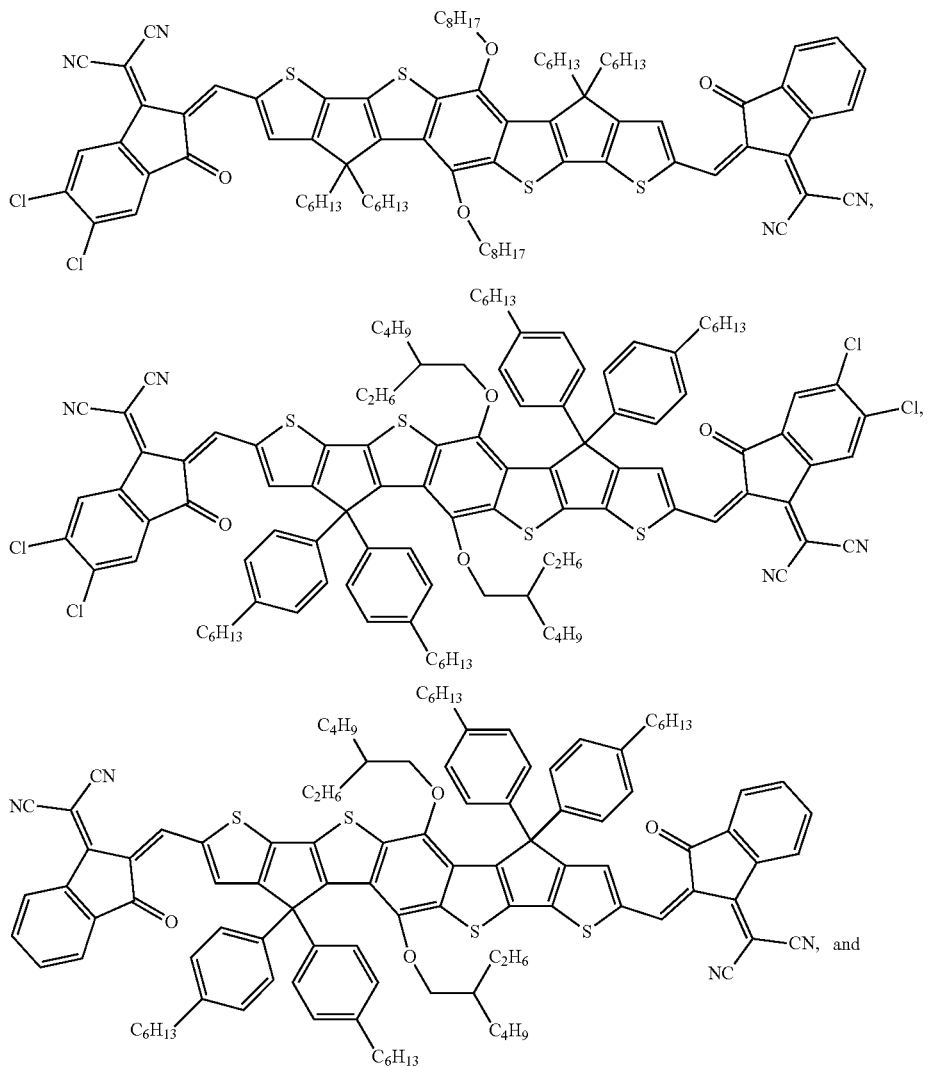

-continued

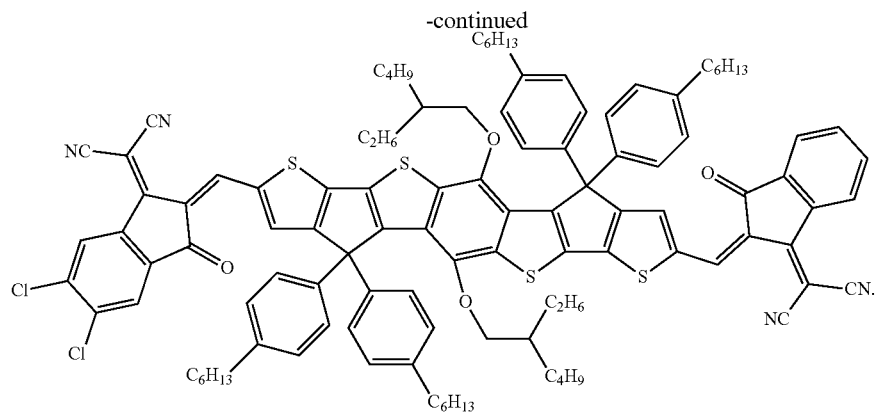

In one embodiment, the device has an open circuit voltage of between about 0.5 V and 1 V. In one embodiment, the device has a fill factor between about 55% and 75%. In one embodiment, the device has a short circuit current of between about 15 mA/cm² and 25 mA/cm². In one embodiment, the device has an external quantum efficiency of between about 65% and 80%.

In another aspect, the present invention relates to a formulation comprising a compound of formula (1) or a stereoisomer thereof:

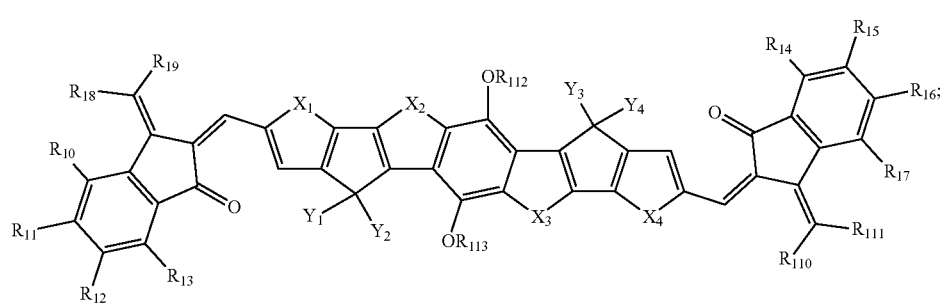

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$ alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof; $R_{18}$, $R_{19}$, $R_{110}$, and $R_{111}$ are each independently an electron withdrawing group selected from the group consisting of: halogen, C(=O)$R_{116}$, $SO_3R_{117}$, cyano, nitro, C($R_{118}$)$_3$, and combinations thereof; $R_{114}$-$R_{117}$ are each independently selected from the group consisting of hydrogen and $C_1$-$C_{20}$ alkyl; $R_{118}$ is a halogen selected from the group consisting of F, Cl, Br, and I; $R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl; $X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 2 depicts an example of various layers of a tandem or multi-junction OPV device.

FIGS. 5A-B, depicts the x-ray scattering patterns extracted from 2D grazing incidence x-ray diffraction (GIXD) images of PCE-10:BT-CIC-IC blends with and without aging. FIG. 5A depicts the in-plane x-ray scattering pattern. FIG. 5B depicts the out-of-plane x-ray scattering pattern. In all figures, Q is the scattering vector.

FIGS. 6A-B, depicts the properties of OPV devices based on PCE-10:BT-IC (1:1.5, w/w), PCE-10:BT-CIC (1:1.5, w/w) and PCE-10:BT-CIC-IC (1:1.5, w/w). FIG. 6A depicts the current-density-voltage characteristics. FIG. 6B depicts the external quantum efficiency (EQE) spectra.

FIG. 8 depicts a table showing the results of the resonant soft X-ray diffraction studies wherein the integrated scattering intensity (ISI) represents the purity of the mixed phase.

FIGS. 9A and 9B, depicts the photostability of a blended active layer. FIG. 9A depicts the structures of PCE-10 and BT-CIC-IC as well as the device used to study the blended layer comprising ITO/1:1.5 ratio of PCE-10:BT-CIC-IC (80 nm)/cover glass. FIG. 9B depicts the photostability results blend of the blended films either aged under continuous illumination from a Xe arc lamp solar simulator at an intensity of 1 kW/m$^2$ or stored in the air under dark.

DETAILED DESCRIPTION

Figure 1:
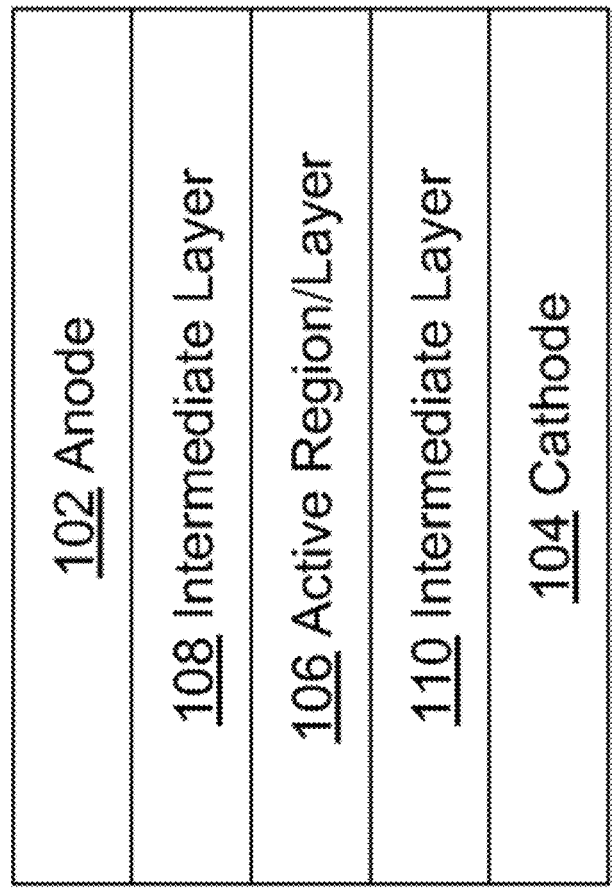
FIG. 1 depicts an example of various layers of a single junction solar cell or organic photovoltaic (OPV) device.

In one aspect, the present invention relates to a non-fullerene acceptor compound for use in OPV devices. In one embodiment, the present invention relates to an asymmetric non-fullerene acceptor compound of use in OPV devices. The present invention also relates to an OPV device comprising a non-fullerene acceptor compound.

Definitions

Unless defined otherwise, all technical and scientific terms used herein have the same meaning as commonly understood by one of ordinary skill in the art to which this invention belongs. The skilled artisan will understand that any methods and materials similar or equivalent to those described herein can be used in the practice or testing of the present invention.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods.

As used herein, the terms "electrode" and "contact" may refer to a layer that provides a medium for delivering photo-generated current to an external circuit or providing a bias current or voltage to the device. That is, an electrode, or contact, provides the interface between the active regions of an organic photosensitive optoelectronic device and a wire, lead, trace or other means for transporting the charge carriers to or from the external circuit. Examples of electrodes include anodes and cathodes, which may be used in a photosensitive optoelectronic device.

As used herein, the terms "donor" and "acceptor" refer to the relative positions of the highest occupied molecular orbital ("HOMO") and lowest unoccupied molecular orbital ("LUMO") energy levels of two contacting but different organic materials. It is energetically favorable, in the absence of an external bias, for electrons at a donor-acceptor junction to move into the acceptor material, and for holes to move into the donor material.

As used herein, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Because ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, the term "band gap" (Eg) of a polymer may refer to the energy difference between the HOMO and the LUMO. The band gap is typically reported in electron-volts (eV). The band gap may be measured from the UV-vis spectroscopy or cyclic voltammetry. A "low band gap" polymer may refer to a polymer with a band gap below 2 eV, e.g., the polymer absorbs light with wavelengths longer than 620 nm.

As used herein, the term "excitation binding energy" (EB) may refer to the following formula: $EB=(M^++M^-)-(M^*+M)$, where $M^+$ and $M^-$ are the total energy of a positively and negatively charged molecule, respectively; $M^*$ and M are the molecular energy at the first singlet state (Si) and ground state, respectively. Excitation binding energy of acceptor or donor molecules affects the energy offset needed for efficient exciton dissociation. In certain examples, the escape yield of a hole increases as the HOMO offset increases. A decrease of exciton binding energy EB for the acceptor molecule leads to an increase of hole escape yield for the same HOMO offset between donor and acceptor molecules.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(=O)OH, trifluoromethyl, —C(=O)O(C$_1$-C$_4$)alkyl, —C(=O)NH$_2$, —SO$_2$NH$_2$, —C(=NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(=O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

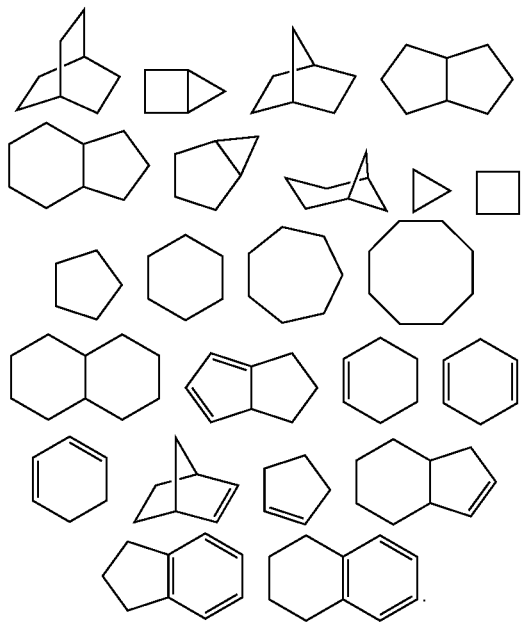

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

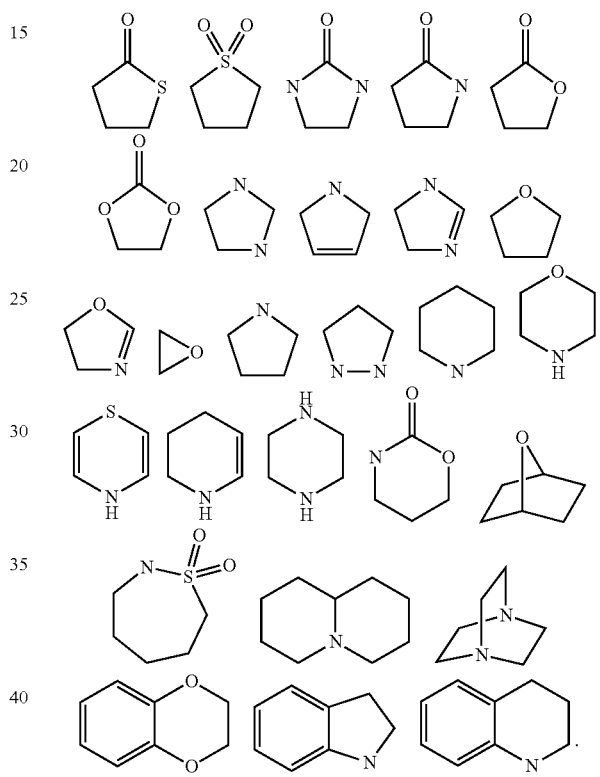

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —CH$_2$CH$_2$-phenyl. In one embodiment, aryl-(C$_1$-C$_3$)alkyl is aryl-CH$_2$— or aryl-CH(CH$_3$)—. The term "substituted aryl-(C$_1$-C$_3$)alkyl" means an aryl-(C$_1$-C$_3$)alkyl functional group in which the aryl group is substituted. Similarly, the term "heteroaryl-(C$_1$-C$_3$)alkyl" means a functional group wherein a one to three carbon alkylene chain is attached to a heteroaryl group, e.g., —CH$_2$CH$_2$-pyridyl. The term "substituted heteroaryl-(C$_1$-C$_3$)alkyl" means a heteroaryl-(C$_1$-C$_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

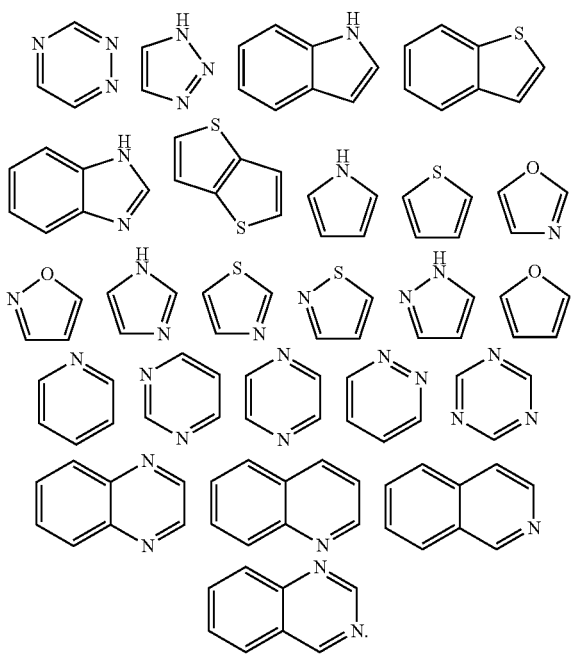

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]2, —OC(=O)N[substituted or unsubstituted alkyl]2, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]2, and —C(NH$_2$)[substituted or unsubstituted alkyl]2. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Non-Fullerene Acceptor Compounds

In one aspect, the present invention relates to a compound of formula (1), or a stereoisomer thereof:

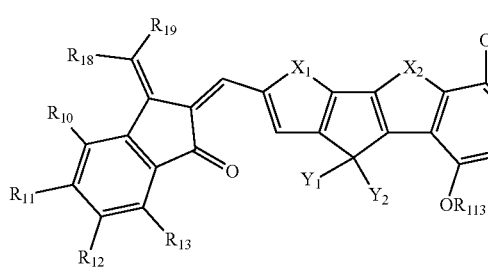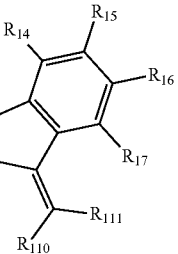

(1)

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$-alkynyl, $C_2$-$C_4$-alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof;

$R_{18}$, $R_{19}$, $R_{110}$, and $R_{111}$ are each independently an electron withdrawing group selected from the group consisting of: halogen, $C(=O)R_{116}$, $SO_3R_{117}$, cyano, nitro, $C(R_{118})_3$, and combinations thereof $R_{114}$-$R_{117}$ are each independently selected from the group consisting of hydrogen and $C_1$-$C_{20}$ alkyl;

$R_{118}$ is a halogen selected from the group consisting of F, Cl, Br, and I;

$R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl;

$X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof.

In one embodiment, $R_{10}$-$R_{13}$ are hydrogen.
In one embodiment, $R_{14}$-$R_{17}$ are hydrogen.
In one embodiment, $R_{11}$ is a halogen. In one embodiment, $R_{11}$ is F. In one embodiment, $R_{11}$ is Cl. In one embodiment, $R_{11}$ is Br. In one embodiment, $R_{11}$ is I.
In one embodiment, $R_{12}$ is a halogen. In one embodiment, $R_{12}$ is F. In one embodiment, $R_{12}$ is Cl. In one embodiment, $R_{12}$ is Br. In one embodiment, $R_{12}$ is I.
In one embodiment, $R_{11}$ and $R_{12}$ are each hydrogen.
In one embodiment, $R_{11}$ is hydrogen and $R_{12}$ is a halogen.
In one embodiment, $R_{11}$ is a halogen and $R_{12}$ is hydrogen.
In one embodiment, $R_{11}$ and $R_{12}$ are each halogen. In one embodiment, $R_{11}$ and $R_{12}$ are each Cl.
In one embodiment, $R_{15}$ is a halogen. In one embodiment, $R_{15}$ is F. In one embodiment, $R_{15}$ is Cl. In one embodiment, $R_{15}$ is Br. In one embodiment, $R_{15}$ is I.
In one embodiment, $R_{16}$ is a halogen. In one embodiment, $R_{16}$ is F. In one embodiment, $R_{16}$ is Cl. In one embodiment, $R_{16}$ is Br. In one embodiment, $R_{16}$ is I.
In one embodiment, $R_{15}$ and $R_{16}$ are each hydrogen.
In one embodiment, $R_{15}$ is hydrogen and $R_{16}$ is a halogen.
In one embodiment, $R_{15}$ is a halogen and $R_{16}$ is hydrogen.
In one embodiment, $R_{15}$ and $R_{16}$ are each halogen. In one embodiment, $R_{15}$ and $R_{16}$ are each Cl.

In one embodiment, $R_{11}$, $R_{12}$, $R_{15}$, and $R_{16}$ are each halogen. In one embodiment, each of $R_{11}$, $R_{12}$, $R_{15}$, and $R_{16}$ are Cl.

In one embodiment, $R_{18}$, $R_{19}$, $R_{110}$, and $R_{111}$ are each cyano.

In one embodiment, $R_{112}$ is a $C_6$-$C_{20}$ alkyl.
In one embodiment, $R_{112}$ is a $C_6$-$C_{20}$ linear alkyl. In one embodiment, $R_{112}$ is a $C_6$ linear alkyl. In one embodiment, $R_{112}$ is a $C_8$ linear alkyl. In one embodiment, $R_{112}$ is a $C_{10}$ linear alkyl. In one embodiment, $R_{112}$ is a $C_{12}$ linear alkyl. In one embodiment, $R_{112}$ is a $C_{14}$ linear alkyl.

In one embodiment, $R_{113}$ is a $C_6$-$C_{20}$ alkyl.
In one embodiment, $R_{113}$ is a $C_6$-$C_{20}$ linear alkyl. In one embodiment, $R_{113}$ is a $C_6$ linear alkyl. In one embodiment, $R_{113}$ is a $C_8$ linear alkyl. In one embodiment, $R_{113}$ is a $C_{10}$ linear alkyl. In one embodiment, $R_{113}$ is a $C_{12}$ linear alkyl. In one embodiment, $R_{113}$ is a $C_{14}$ linear alkyl.

In one embodiment, $R_{112}$ is a $C_6$-$C_{20}$ branched alkyl. In one embodiment, $R_{112}$ is a $C_6$ branched alkyl. In one embodiment, $R_{112}$ is a $C_8$ branched alkyl. In one embodiment, $R_{112}$ is a $C_{10}$ branched alkyl. In one embodiment, $R_{112}$ is a $C_{12}$ branched alkyl. In one embodiment, $R_{112}$ is a $C_{14}$ branched alkyl.

In one embodiment, $R_{112}$ is

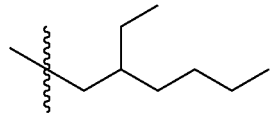

In one embodiment, $R_{113}$ is a $C_6$-$C_{20}$ branched alkyl. In one embodiment, $R_{113}$ is a $C_6$ branched alkyl. In one embodiment, $R_{113}$ is a $C_8$ branched alkyl. In one embodiment, $R_{113}$ is a $C_{10}$ branched alkyl. In one embodiment, $R_{113}$ is a $C_{12}$ branched alkyl. In one embodiment, $R_{113}$ is a $C_{14}$ branched alkyl.

In one embodiment, $R_{113}$ is

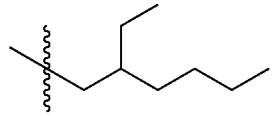

In one embodiment, $R_{112}$ is a substituted $C_6$-$C_{10}$ aryl. In one embodiment, $R_{112}$ is a substituted $C_6$ aryl. In one embodiment, $R_{112}$ is a $C_6$ aryl substituted with one or more $C_1$-$C_{12}$ alkyl groups. In one embodiment, $R_{112}$ is a $C_6$ aryl substituted with one or more $C_1$-$C_{12}$ linear alkyl groups. In one embodiment, $R_{112}$ is a $C_6$ aryl substituted with one or more $C_1$-$C_{12}$ branched alkyl groups.

In one embodiment, $R_{112}$ is

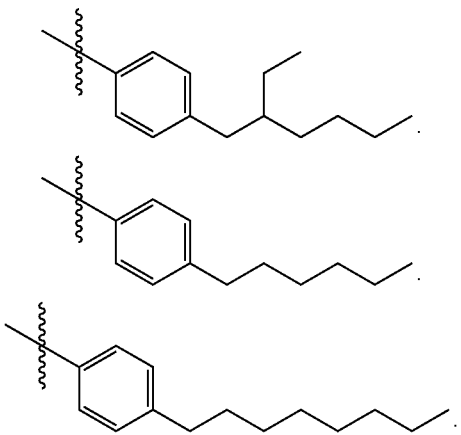

In one embodiment, $R_{112}$ is

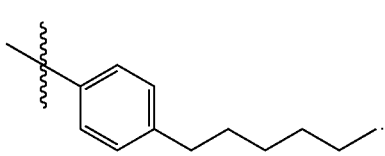

In one embodiment, $R_{112}$ is

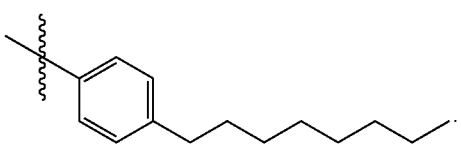

In one embodiment, $R_{113}$ is a substituted $C_6$-$C_{10}$ aryl. In one embodiment, $R_{113}$ is a substituted $C_6$ aryl. In one embodiment, $R_{113}$ is a $C_6$ aryl substituted with one or more $C_1$-$C_{12}$ alkyl groups. In one embodiment, $R_{113}$ is a $C_6$ aryl substituted with one or more $C_1$-$C_{12}$ linear alkyl groups. In one embodiment, $R_{113}$ is a $C_6$ aryl substituted with one or more $C_1$-$C_{12}$ branched alkyl groups.

In one embodiment, $R_{113}$ is

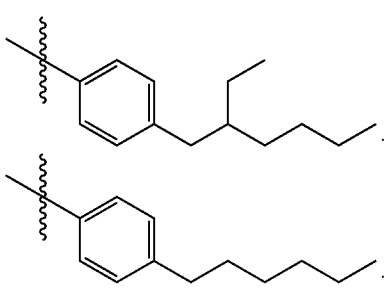

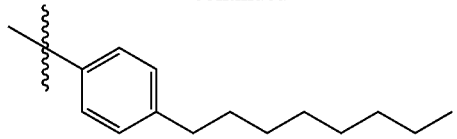

In one embodiment, $R_{113}$ is

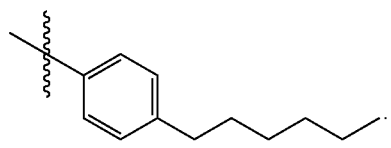 [SMILES: *c1ccc(CCCCCC)cc1]

In one embodiment, $R_{113}$ is

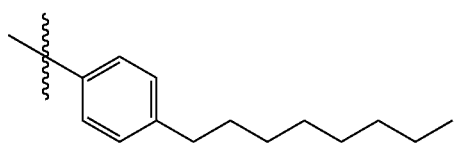

In one embodiment, $Y_1$ is a $C_6$-$C_{20}$ alkyl.

In one embodiment, $Y_1$ is a $C_6$-$C_{20}$ linear alkyl. In one embodiment, $Y_1$ is a $C_6$ linear alkyl. In one embodiment, $Y_1$ is a $C_8$ linear alkyl. In one embodiment, $Y_1$ is a $C_{10}$ linear alkyl. In one embodiment, $Y_1$ is a $C_{12}$ linear alkyl. In one embodiment, $Y_1$ is a $C_{14}$ linear alkyl.

In one embodiment, $Y_1$ is a $C_6$-$C_{20}$ branched alkyl. In one embodiment, $Y_1$ is a $C_6$ branched alkyl. In one embodiment, $Y_1$ is a $C_8$ branched alkyl. In one embodiment, $Y_1$ is a $C_{10}$ branched alkyl. In one embodiment, $Y_1$ is a $C_{12}$ branched alkyl. In one embodiment, $Y_1$ is a $C_{14}$ branched alkyl.

In one embodiment, $Y_1$ is

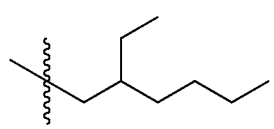

In one embodiment, $Y_1$ is a substituted $C_6$-$C_{10}$ aryl. In one embodiment, $Y_1$ is a substituted $C_6$ aryl. In one embodiment, $Y_1$ is a $C_6$ aryl substituted with one or more $C_1$-$C_{12}$ alkyl groups. In one embodiment, $Y_1$ is a $C_6$ aryl substituted with one or more $C_1$-$C_{12}$ linear alkyl groups. In one embodiment, $Y_1$ is a $C_6$ aryl substituted with one or more $C_1$-$C_{12}$ branched alkyl groups.

In one embodiment, $Y_1$ is

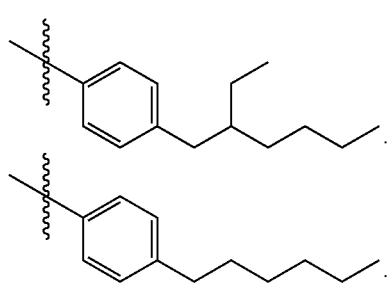

-continued

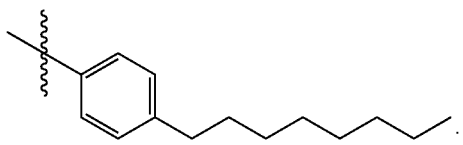 [SMILES: *c1ccc(CCCCCCCC)cc1]

In one embodiment, $Y_1$ is

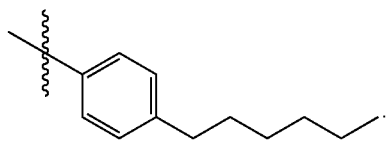 [SMILES: *c1ccc(CCCCCC)cc1]

In one embodiment, $Y_1$ is

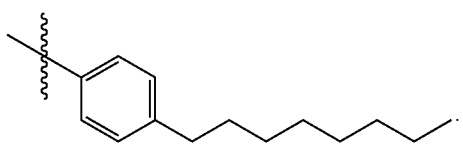

In one embodiment, $Y_2$ is a —$C_6$-$C_{20}$ alkyl.

In one embodiment, $Y_2$ is a $C_6$-$C_{20}$ linear alkyl. In one embodiment, $Y_2$ is a $C_6$ linear alkyl. In one embodiment, $Y_2$ is a $C_8$ linear alkyl. In one embodiment, $Y_2$ is a $C_{10}$ linear alkyl. In one embodiment, $Y_2$ is a $C_{12}$ linear alkyl. In one embodiment, $Y_2$ is a $C_{14}$ linear alkyl.

In one embodiment, $Y_2$ is a $C_6$-$C_{20}$ branched alkyl. In one embodiment, $Y_2$ is a $C_6$ branched alkyl. In one embodiment, $Y_2$ is a $C_8$ branched alkyl. In one embodiment, $Y_2$ is a $C_{10}$ branched alkyl. In one embodiment, $Y_2$ is a $C_{12}$ branched alkyl. In one embodiment, $Y_2$ is a $C_{14}$ branched alkyl.

In one embodiment, $Y_2$ is

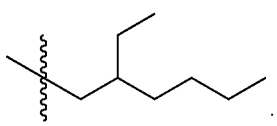 [SMILES: *CC(CC)CCCC]

In one embodiment, $Y_2$ is a substituted $C_6$-$C_{10}$ aryl. In one embodiment, $Y_2$ is a substituted $C_6$ aryl. In one embodiment, $Y_2$ is a $C_6$ aryl substituted with one or more $C_1$-$C_{12}$ alkyl groups. In one embodiment, $Y_2$ is a $C_6$ aryl substituted with one or more $C_1$-$C_{12}$ linear alkyl groups. In one embodiment, $Y_2$ is a $C_6$ aryl substituted with one or more $C_1$-$C_{12}$ branched alkyl groups.

In one embodiment, $Y_2$ is

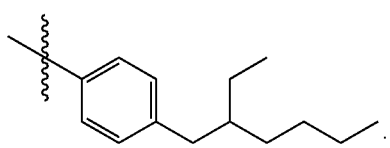

-continued

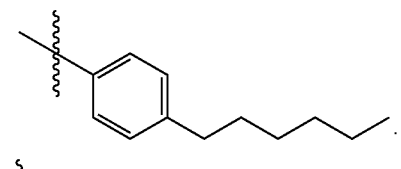

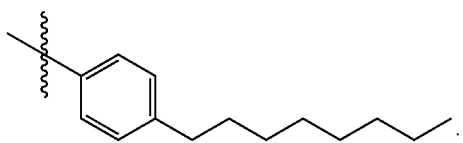 [SMILES: *c1ccc(CCCCCCCC)cc1]

In one embodiment, $Y_2$ is

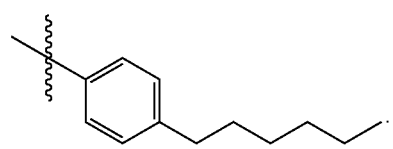 [SMILES: *c1ccc(CCCCCC)cc1]

In one embodiment, $Y_2$ is

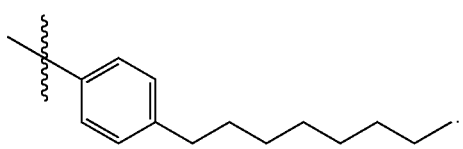

In one embodiment, $Y_3$ is a $C_6$-$C_{20}$ alkyl.

In one embodiment, $Y_3$ is a $C_6$-$C_{20}$ linear alkyl. In one embodiment, $Y_3$ is a $C_6$ linear alkyl. In one embodiment, $Y_3$ is a $C_8$ linear alkyl. In one embodiment, $Y_3$ is a $C_{10}$ linear alkyl. In one embodiment, $Y_3$ is a $C_{12}$ linear alkyl. In one embodiment, $Y_3$ is a $C_{14}$ linear alkyl.

In one embodiment, $Y_3$ is a $C_6$-$C_{20}$ branched alkyl. In one embodiment, $Y_3$ is a $C_6$ branched alkyl. In one embodiment, $Y_3$ is a $C_8$ branched alkyl. In one embodiment, $Y_3$ is a $C_{10}$ branched alkyl. In one embodiment, $Y_3$ is a $C_{12}$ branched alkyl.

In one embodiment, $Y_3$ is a $C_{14}$ branched alkyl.

In one embodiment, $Y_3$ is

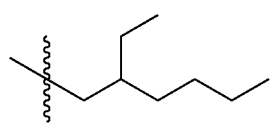

In one embodiment, $Y_3$ is a substituted $C_6$-$C_{10}$ aryl. In one embodiment, $Y_3$ is a substituted $C_6$ aryl. In one embodiment, $Y_3$ is a $C_6$ aryl substituted with one or more $C_1$-$C_{12}$ alkyl groups. In one embodiment, $Y_3$ is a $C_6$ aryl substituted with one or more $C_1$-$C_{12}$ linear alkyl groups. In one embodiment, $Y_3$ is a $C_6$ aryl substituted with one or more $C_1$-$C_{12}$ branched alkyl groups.

In one embodiment, $Y_3$ is

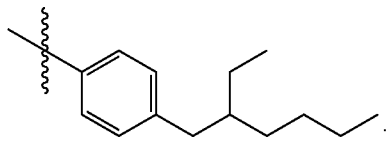

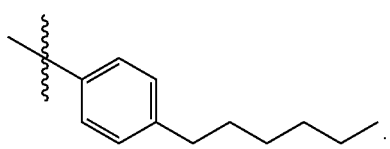

In one embodiment, $Y_3$ is

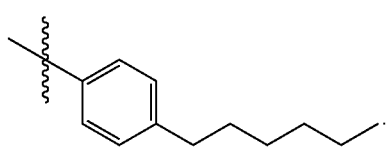 [SMILES: *c1ccc(CCCCCC)cc1]

In one embodiment, $Y_3$ is

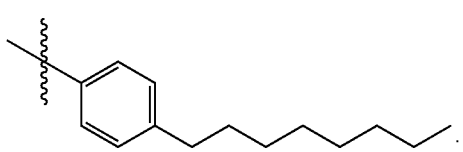 [SMILES: *c1ccc(CCCCCCCC)cc1]

In one embodiment, $Y_4$ is a $C_6$-$C_{20}$ alkyl.

In one embodiment, $Y_4$ is a $C_6$-$C_{20}$ linear alkyl. In one embodiment, $Y_4$ is a $C_6$ linear alkyl. In one embodiment, $Y_4$ is a $C_8$ linear alkyl. In one embodiment, $Y_4$ is a $C_{10}$ linear alkyl. In one embodiment, $Y_4$ is a $C_{12}$ linear alkyl. In one embodiment, $Y_4$ is a $C_{14}$ linear alkyl.

In one embodiment, $Y_4$ is a $C_6$-$C_{20}$ branched alkyl. In one embodiment, $Y_4$ is a $C_6$ branched alkyl. In one embodiment, $Y_4$ is a $C_8$ branched alkyl. In one embodiment, $Y_4$ is a $C_{10}$ branched alkyl. In one embodiment, $Y_4$ is a $C_{12}$ branched alkyl. In one embodiment, $Y_4$ is a $C_{14}$ branched alkyl.

In one embodiment, $Y_4$ is

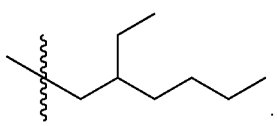 [SMILES: *CC(CC)CCCC]

In one embodiment, $Y_4$ is a substituted $C_6$-$C_{10}$ aryl. In one embodiment, $Y_4$ is a substituted $C_6$ aryl. In one embodiment, $Y_4$ is a $C_6$ aryl substituted with one or more $C_1$-$C_{12}$ alkyl groups. In one embodiment, $Y_4$ is a $C_6$ aryl substituted with one or more $C_1$-$C_{12}$ linear alkyl groups. In one embodiment, $Y_4$ is a $C_6$ aryl substituted with one or more $C_1$-$C_{12}$ branched alkyl groups.

In one embodiment, $Y_4$ is

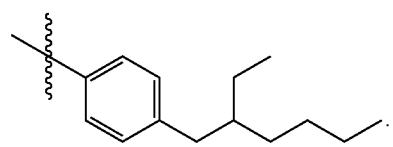

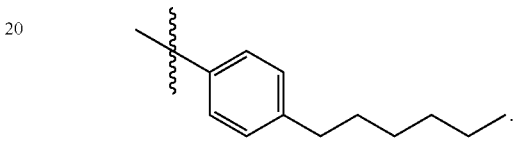

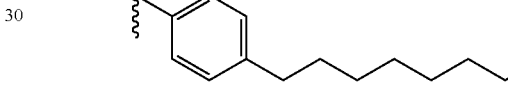

In one embodiment, $Y_4$ is

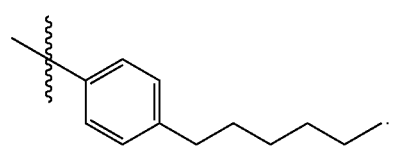 [SMILES: *c1ccc(CCCCCC)cc1]

In one embodiment, $Y_4$ is

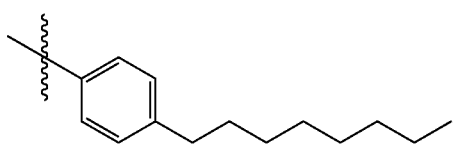

In one embodiment, each of $X^1$-$X^4$ are S. In one embodiment, each of $X^1$—$X^4$ are O. In one embodiment, each of $X^1$—$X^4$ are Se. In one embodiment, $X^1$ and $X^4$ are S and $X^2$ and $X^3$ are O. In one embodiment, $X^1$ and $X^4$ are O and $X^2$ and $X^3$ are S. In one embodiment, $X^1$ and $X^4$ are S and $X^2$ and $X^3$ are Se. In one embodiment, $X^1$ and $X^4$ are Se and $X^3$ are S. In one embodiment, $X^1$ and $X^4$ are O and $X^2$ and $X^3$ are Se. In one embodiment, $X^1$ and $X^4$ are Se and $X^2$ and $X^3$ are O.

In one embodiment, the compound of formula (1) is symmetric. In one embodiment, the compound of formula (1) is a symmetric acceptor. In one embodiment, the symmetric compound of formula (1) is selected from the group consisting of: consisting of:

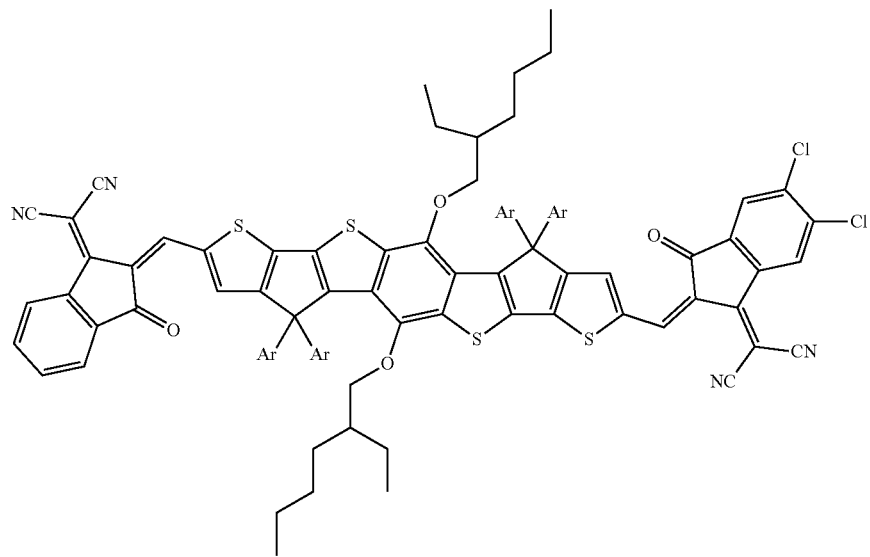
BT-CIC-IC
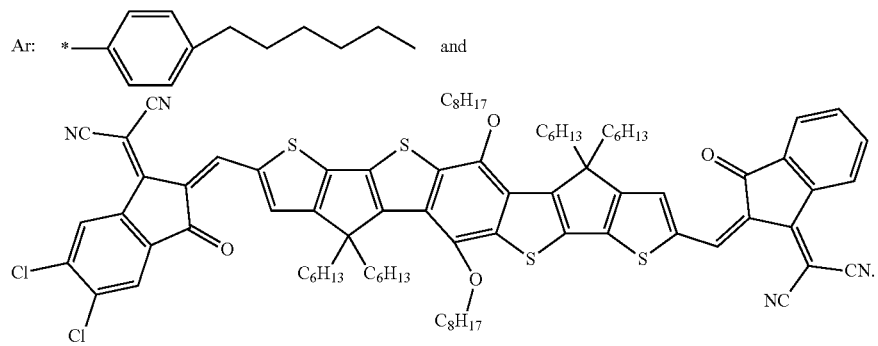
In one embodiment, the compound of formula (1) is symmetric. In one embodiment, the compound of formula (1) is a symmetric acceptor. In one embodiment, the symmetric compound of formula (1) is selected from the group consisting of:
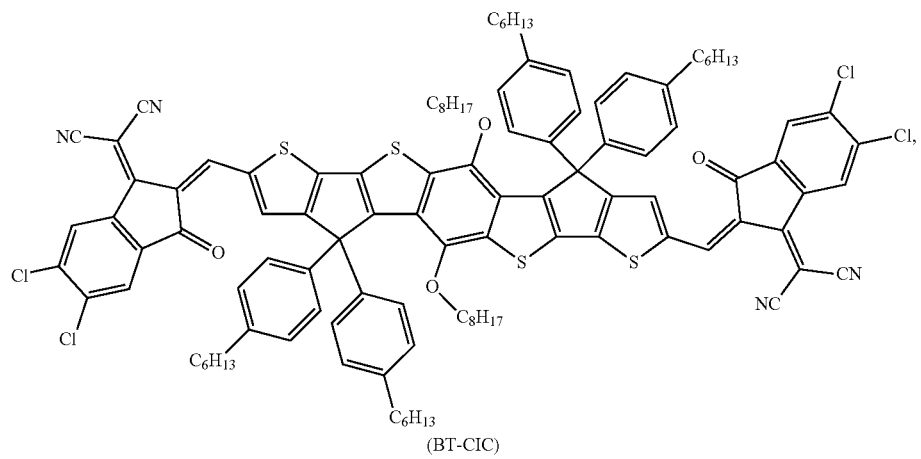
(BT-CIC)

-continued
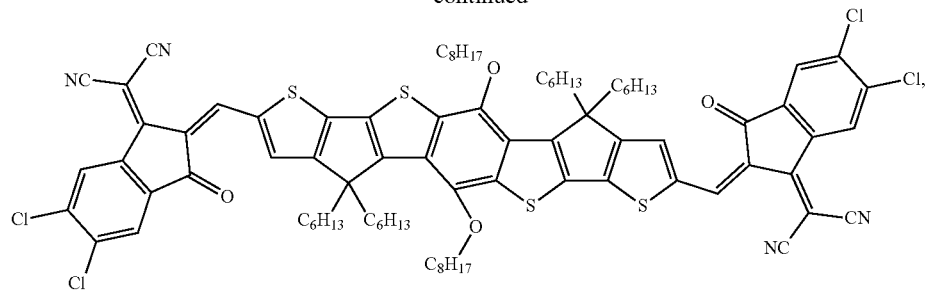
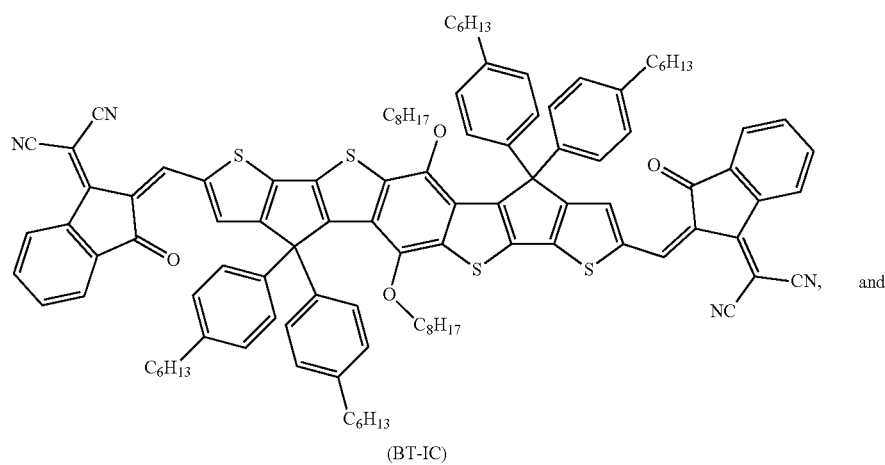
(BT-IC)
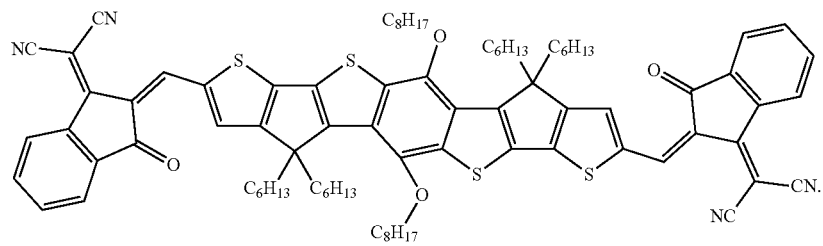
In one embodiment, BT-CIC has a structure
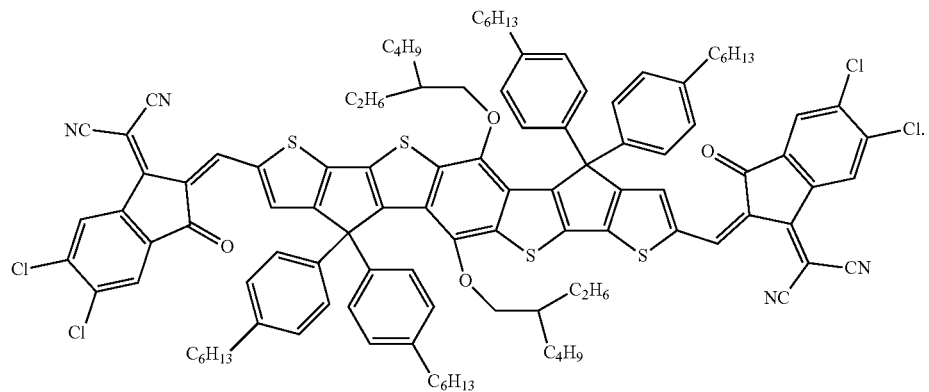

In one embodiment, BT-IC has a structure

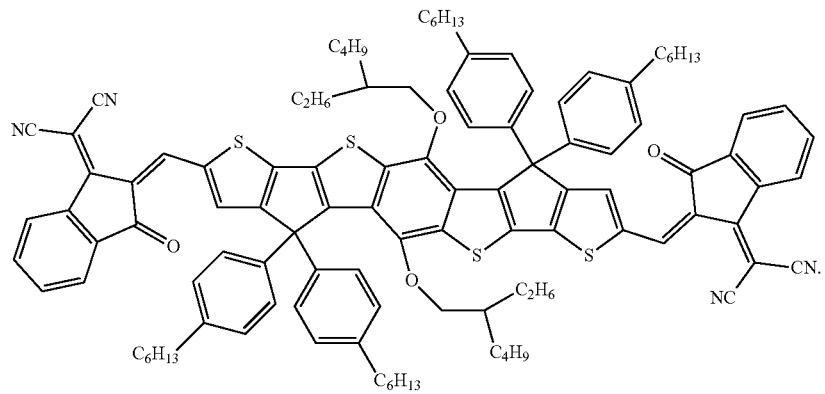

In one embodiment, the aromatic groups $Ar^1$, $Ar^2$, and $Ar^3$, in combination with benzene ring(s) within the non-fullerene acceptor provide a coplanar ring structure having a conjugation length of seven to fifteen rings. In one embodiment, the overall length of the non-fullerene acceptor may be at least 20 angstroms, 25 angstroms, 30 angstroms, 35 angstroms, 40 angstroms, 50 angstroms, or between 20-50 angstroms, 25 40 angstroms, or 25-35 angstroms.

In one embodiment, the non-fullerene acceptor comprises BT-IC. BT-IC has planar structure with a small torsion angle<1° and consequently, a high electron mobility. However, the absorption of BT-IC does not extend to wavelengths λ>850 nm. This leaves a potential opening for further improvement in OPV device performance. In one embodiment, the non-fullerene acceptor comprises BT-CIC. This structure provides a narrow absorption band confined to the near-infrared spectrum through the introduction of high electron affinity halogen atoms (e.g., chlorine atoms). BT-CIC comprises four chlorine atoms positioned in the 5,6-positions of the 2-(3-oxo-2,3-dihydroinden-1-ylidene) malononitrile. The design is advantageous as it avoids significant issues of previously reported in chlorinated molecules with non-specific atomic site positioning (and hence property variability).

The non-fullerene acceptor compositions disclosed herein provide certain improved characteristics over conventional acceptor compositions. For example, the non-fullerene acceptors disclosed herein may provide an increased electron density for the donor molecule, a reduced electron density for the acceptor molecule, and an increased conjugation length of the A-D-A molecule.

In one embodiment, the electron-withdrawing halogen (e.g., Cl) atoms effectively lower the energy gap by enhancing the intramolecular charge transfer and derealization of π-electrons into the unoccupied, atomic 3d orbitals. In one embodiment, intermolecular interactions of Cl—S and Cl—Cl result in ordered molecular stacks in the donor-acceptor blend films.

In one embodiment, the non-fullerene acceptor compounds of formula (1) have an energy gap of less than 2 eV, less than 1.5 eV, less than 1.4 eV, less than 1.3 eV, less than 1.2 eV, less than 1.1 eV, less than 1 eV, between 1-2 eV, between 1-1.5 eV, between 1.1-1.4 eV, or between 1.2-1.3 eV.

In one embodiment, the non-fullerene acceptors of the present invention are used in an organic A-D-A heterojunction wherein the effective separation of electron and hole may be controlled by the molecular length and electronegativity of the electron donating or withdrawing group. In one embodiment, the exciton binding energy decreases as the molecular length increases for various acceptor molecules. An increase of the extent of exciton distribution, i.e. exciton radius, over the conjugated carbon chain will increase the effective separation between electron and hole. In one embodiment, the effective separation of electron and hole is also affected by the electronegativity of A or D components. Introducing a halogen into the electron-deficient group and/or adding an oxygen or sulfide to the electron-rich group will twist the electron/hole density distribution, and changes the effective distance of electron and hole, and therefore reduce the exciton binding energy.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$ $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$ is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The compounds of the present invention may be synthesized using techniques well-known in the art of organic synthesis. The starting materials and intermediates required for the synthesis may be obtained from commercial sources or synthesized according to methods known to those skilled in the art.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1 5 and Supplementals (Elsevier Science Publishers, 1989); Organic Reactions, Volumes 1 40 (John Wiley and Sons, 1991), Larock's Comprehensive Organic Transformations (VCH Publishers Inc., 1989), March, Advanced Organic Chemistry 4$^{th}$ Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference in their entirety). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

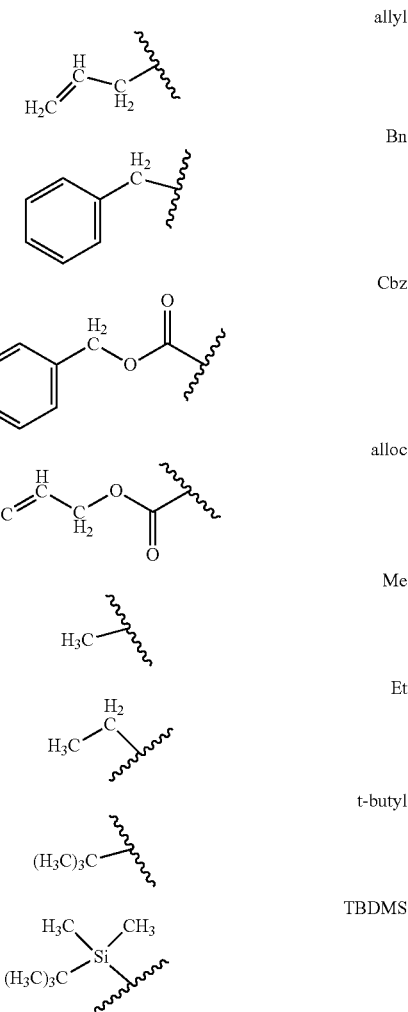

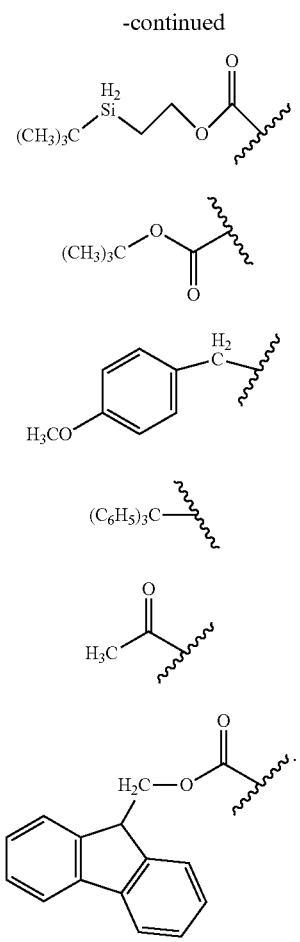

Other protecting groups, plus a detailed description of techniques applicable to the creation of protecting groups and their removal are described in Greene & Wuts, Protective Groups in Organic Synthesis, 3rd Ed., John Wiley & Sons, New York, NY, 1999, and Kocienski, Protective Groups, Thieme Verlag, New York, NY, 1994, which are incorporated herein by reference for such disclosure.

In one embodiment, the present invention relates to a formulation comprising a compound of formula (1).

OPV Devices

In one aspect, the invention relates to an OPV device comprising a compound of formula (1). In one embodiment, the OPV device includes an anode; a cathode; and an active material positioned between the anode and cathode, wherein the active material comprises a non-fullerene acceptor and a donor. In one embodiment, the non-fullerene acceptor comprises a compound of formula (1). In one embodiment, the non-fullerene acceptor comprises an asymmetric compound of formula (1). In one embodiment, the non-fullerene acceptor comprises a symmetric compound of formula (1).

In one embodiment, the OPV device comprises a single junction organic photovoltaic device 100 having a non-fullerene acceptor compound (FIG. 1). In one embodiment, the OPV device comprises two electrodes having an anode 102 and a cathode 104 in superposed relation, at least one donor composition, and at least one acceptor composition, wherein the donor-acceptor material or active layer 106 is positioned between the two electrodes 102 and 104. In one embodiment, one or more intermediate layers 108 may be positioned between the anode 102 and the active layer 106. Additionally, or alternatively, one or more intermediate layers 110 may be positioned between the active layer 106 and cathode 104.

In one embodiment, the anode 102 comprises a conducting oxide, thin metal layer, or conducting polymer. In one embodiment, the anode 102 comprises a conductive metal oxide. Exemplary conductive metal oxides include, but are not limited to, indium tin oxide (ITO), tin oxide (TO), gallium indium tin oxide (GITO), zinc oxide (ZO), and zinc indium tin oxide (ZITO). In one embodiment, the anode 102 comprises a metal layer. Exemplary metals for the metal layer include, but are not limited to, Ag, Au, Pd, Pt, Ti, V, Zn, Sn, Al, Co, Ni, Cu, Cr, and combinations thereof. In one embodiment, the metal layer comprises a thin metal layer. In one embodiment, the anode 102 comprises a conductive polymer. Exemplary conductive polymers include, but are not limited to, polyanaline (PANI), or 3,4-polyethyl-enedi-oxythiophene:polystyrenesulfonate (PEDOT:PSS). In one embodiment, thickness of the anode 102 is between about 0.1-100 nm. In one embodiment, thickness of the anode 102 is between about 1-10 nm. In one embodiment, thickness of the anode 102 is between about 0.1-10 nm. In one embodiment, thickness of the anode 102 is between about 10-100 nm.

In one embodiment, the cathode 104 comprises a conducting oxide, a metal layer, or conducting polymer. Exemplary conducting oxide, metal layers, and conducting polymers are described elsewhere herein. In one embodiment, the cathode comprises a thin metal layer. In one embodiment, the cathode 104 comprises a metal or metal alloy. In one embodiment, the cathode 104 may comprise Ca, Al, Mg, Ti, W, Ag, Au, or another appropriate metal, or an alloy thereof. In one embodiment, the thickness of the cathode 104 is between about 0.1-100 nm. In one embodiment, the thickness of the cathode 104 is between about 1-10 nm. In one embodiment, the thickness of the cathode 104 is between about 0.1-10 nm. In one embodiment, the thickness of the cathode 104 is between about 10-100 nm.

In one embodiment, the OPV device may comprise one or more charge collecting/transporting intermediate layers positioned between an electrode 102, 104, and the active region or layer 106. In one embodiment, the OPV device comprises intermediate layer 108. In one embodiment, the OPV device comprises intermediate layer 110. In one embodiment, the OPV device comprises both intermediate layers 108 and 110. In one embodiment, intermediate layer 108 comprises a metal oxide. In one embodiment, intermediate layer 110 comprises a metal oxide. Exemplary metal oxides include, but are not limited to, $MoO_3$, $V_2O_5$, ZnO, and $TiO_2$. In one embodiment, the first intermediate layer 108 has the same composition as the second intermediate layer 110. In one embodiment, the first intermediate layer 108 and the second intermediate layer 110 have different compositions. In one embodiment, the thickness of intermediate layer 108 and intermediate layer 110 are each independently between about 0.1-100 nm. In one embodiment, the thickness of intermediate layer 108 and intermediate layer 110 are each independently between about 1-10 nm. In one embodiment, the thickness of intermediate layer 108 and intermediate layer 110 are each independently between about 0.1-10 nm. In one embodiment, the thickness of intermediate layer 108 and intermediate layer 110 are each independently between about 10-100 nm.

In one embodiment, the active region or layer 106 positioned between the electrodes 102 and 104 comprises a composition or molecule having an acceptor and a donor. In one embodiment, the acceptor comprises a non-fullerene acceptor. In one embodiment, the non-fullerene acceptor comprises a compound of formula (1). In one embodiment, the non-fullerene acceptor comprises an asymmetric compound of formula (1). In one embodiment, the non-fullerene acceptor comprises a symmetric compound of formula (1). In one embodiment, the composition is arranged as acceptor-donor-acceptor (A-D-A).

In one embodiment, the OPV device comprises various layers of a tandem or multi junction photovoltaic device 200 having a non-fullerene acceptor compound (FIG. 2). In one embodiment, the OPV device comprises two electrodes having an anode 202 and a cathode 204 in superposed relation, at least one donor composition, and at least one acceptor composition positioned within a plurality of active layers or regions 206A and 206B between the two electrodes 202 and 204. While only two active layers or regions 206A and 206B are depicted in FIG. 2, additional active layers or regions are also possible. In one embodiment, the anode 202 and the cathode 204 each independently comprise a conducting oxide, thin metal layer, or conducting polymer. Exemplary conducting oxides, metal layers, and conducting polymers are described elsewhere herein.

In one embodiment, the OPV device comprises one or more intermediate layers 208 positioned between the anode 202 and a first active layer 206A. Additionally, or alternatively, at least one intermediate layer 210 may be positioned between the second active layer 206B and cathode 204. In one embodiment, the OPV device comprises one or more intermediate layers 212 positioned between the first active layer 206A and the second active layer 206B. In one embodiment, the OPV device comprises intermediate layer 208. In one embodiment, the OPV device comprises intermediate layer 210. In one embodiment, the OPV device comprises intermediated layer 212. In one embodiment, the OPV device comprises both intermediate layers 208 and 210. In one embodiment, the OPV device comprises both intermediate layers 208 and 212. In one embodiment, the OPV device comprises both intermediate layers 210 and 212. In one embodiment, the OPV device comprises intermediate layers 208, 210, and 212. In one embodiment, intermediate layer 208 comprises a metal oxide. In one embodiment, intermediate layer 210 comprises a metal oxide. In one embodiment, intermediate layer 212 comprises a metal oxide. Exemplary metal oxides are described elsewhere herein. Exemplary thicknesses for intermediate layers 208, 210, and 212 are described elsewhere herein.

In one embodiment, the active region or layer 206A and 206B positioned between the electrodes comprises a composition or molecule having an acceptor and a donor. In one embodiment, the acceptor comprises a non-fullerene acceptor. In one embodiment, the non-fullerene acceptor comprises a compound of formula (1). In one embodiment, the non-fullerene acceptor comprises an asymmetric compound of formula (1). In one embodiment, the non-fullerene acceptor comprises a symmetric compound of formula (1). In one embodiment, the composition is arranged as acceptor-donor-acceptor (A-D-A).

In one embodiment, the donor material or composition within the active layer or region 106 comprises a low energy band gap polymer composition. In one embodiment, the donor material or composition within each active layer or region 206A and 206B independently comprises a low energy band gap polymer composition. In one embodiment, the donor composition comprises a polymer having a band gap of less than 2 eV. In one embodiment, the low band gap polymer donor comprises poly[4,8-bis(5-(2-ethylhexyl)thiophen-2-yl)benzo [1,2-b:4,5-b']dithiophene-co-3-fluorothieno [3,4-b]thiophene-2-carboxylate, or a derivative thereof. In one embodiment, the low band gap polymer donor comprises poly(3-hexylthiophene) or a derivative thereof. In one embodiment, the low band gap polymer donor comprises poly[N-9'-heptadecanyl-2,7-carbazole-alt-5,5-(4',7'-di-2-thienyl-2',1',3'-benzothiadazole)] (i.e. PCDTBT), or a derivative thereof.

In one embodiment, the low energy band gap polymer is selected from the group consisting of:

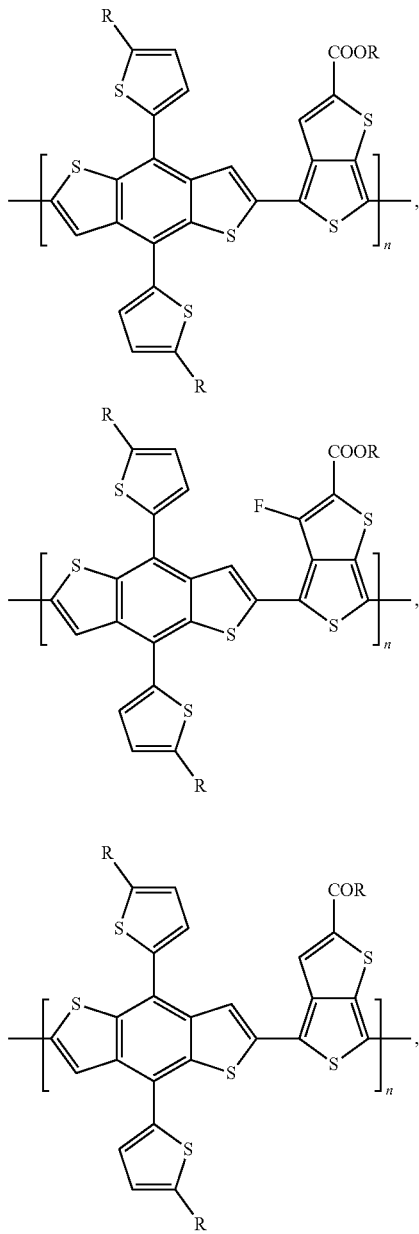

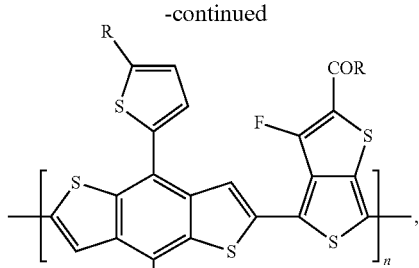
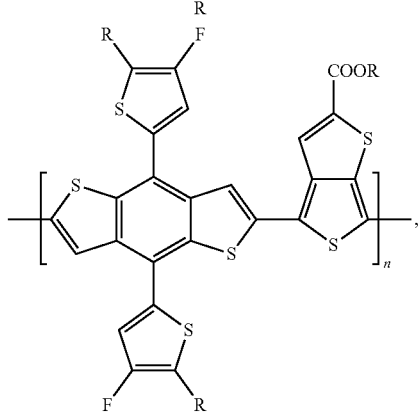
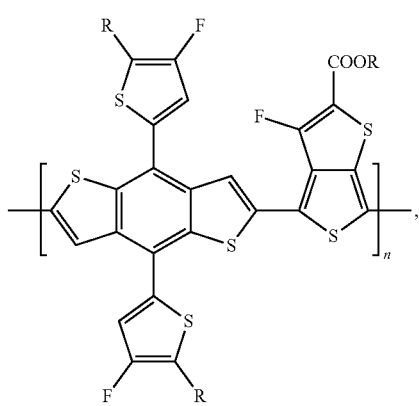
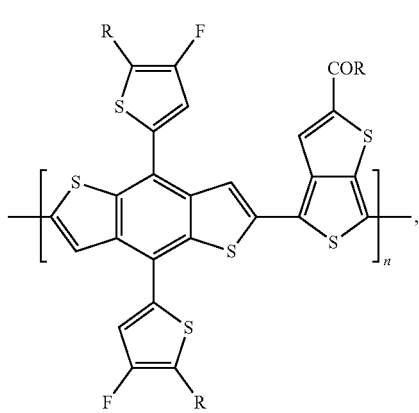
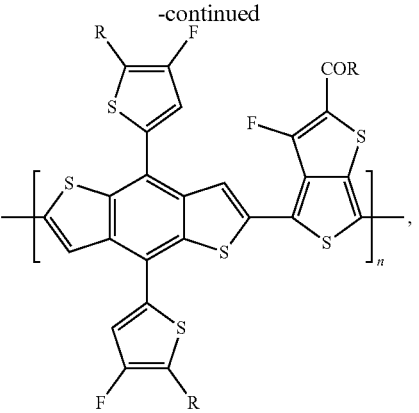

-continued

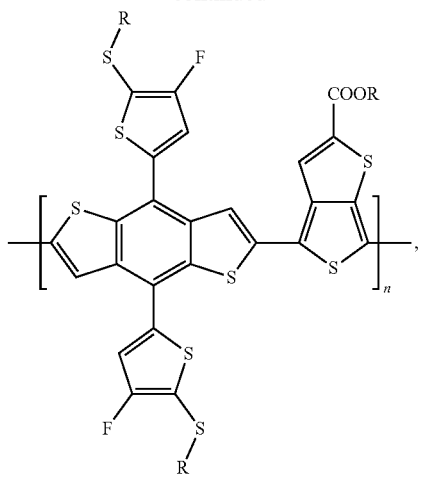

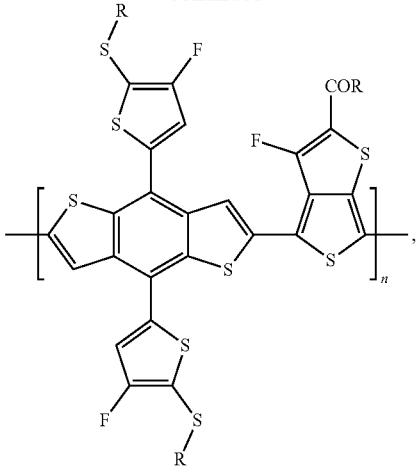

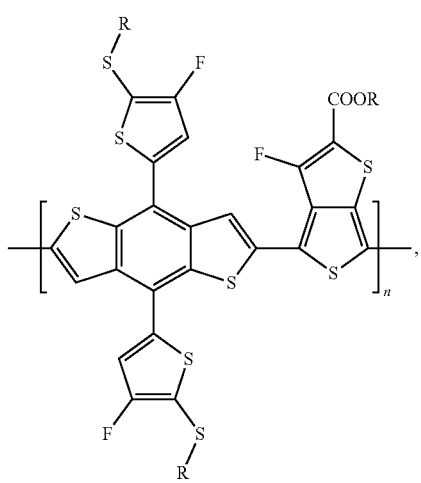

and derivatives thereof; wherein each R is independently a $C_1$-$C_{20}$ alkyl; and n is the degree of polymerization. In one embodiment each R is independently a $C_1$-$C_{20}$ linear alkyl. In one embodiment each R is independently a $C_1$-$C_{20}$ branched alkyl. In one embodiment, each R is independently selected from the group consisting of methyl, ethyl, n-propyl, isopropyl, isobutyl, n-butyl, sec-butyl, tert-butyl, isopentyl, n-pentyl, neopentyl, n-hexyl, 2-ethylhexyl, and octyl. In In one embodiment, each R represents 2-ethylhexyl. In one embodiment, n is between about 1-1000. In one embodiment, n is between about 1-100. In one embodiment, n is between about 10-1000.

In one embodiment, the donor is

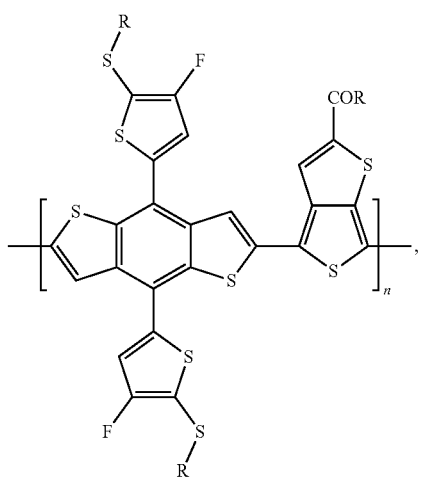

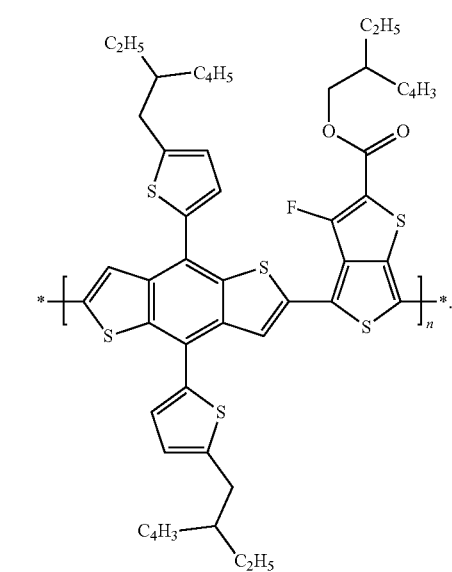

In one embodiment, an OPV device comprising a non-fullerene acceptor of formula (1) demonstrates improved performance properties over OPV devices comprising fullerene acceptors. In one embodiment, the OPV device comprises a fullerene acceptor of formula (1) having an electron-withdrawing halogen. In one embodiment, an OPV device comprising a halogen-containing non-fullerene acceptor of formula (1) demonstrates improved performance properties compared to devices comprising a non-fullerene acceptor that does not have an electron-withdrawing halogen. In one embodiment, the OPV device comprising a halogen-containing non-fullerene acceptor of formula (1) has an improved power conversion efficiency (PCE). In one embodiment, an OPV device comprising a halogen-containing non-fullerene acceptor of formula (1) having an electron-withdrawing halogen has a PCE between about 1% and 30%. In one embodiment, the PCE is between about 1% and 25%. In one embodiment, the PCE is between about 1% and 20%. In one embodiment, the PCE is between about 1% and 15%. In one embodiment, the PCE is between about 5% and 15%. In one embodiment, the halogen-containing non-fullerene acceptor of formula (1) comprises BT-CIC. In one embodiment, the halogen-containing non-fullerene acceptor of formula (1) comprises BT-CIC-IC.

In one embodiment, an OPV device comprising a non-fullerene acceptor of formula (1) has a high open circuit voltage ($V_{OC}$). In one embodiment, the $V_{OC}$ is at least about 0.5 V, at least about 0.6 V, at least about 0.7 V, at least about 0.8 V, at least about 0.9 V, or at least about 1 V. In one embodiment, the $V_{OC}$ is between about 0.1 V and 5 V. In one embodiment, the $V_{OC}$ is between about 0.1 V and 4.5 V. In one embodiment, the $V_{OC}$ is between about 0.1 V and 4 V. In one embodiment, the $V_{OC}$ is between about 0.1 V and 3.5 V. In one embodiment, the $V_{OC}$ is between about 0.1 V and 3 V. In one embodiment, the $V_{OC}$ is between about 0.1 V and 2.5 V. In one embodiment, the $V_{OC}$ is between about 0.1 V and 2 V. In one embodiment, the $V_{OC}$ is between about 0.1 V and 1.5 V. In one embodiment, the $V_{OC}$ is between about 0.1 V and 1 V. In one embodiment, the $V_{OC}$ is between about 0.5 V and 1 V. In one embodiment, the device having a high $V_{OC}$ comprises the non-fullerene acceptor compound BT-IC. In one embodiment, the device having a high $V_{OC}$ comprises the non-fullerene acceptor compound BT-CIC. In one embodiment, the device having a high $V_{OC}$ comprises the non-fullerene acceptor compound BT-CIC-IC.

In one embodiment, an OPV device comprising a non-fullerene acceptor of formula (1) has a high fill factor (FF). In one embodiment, the FF is at least about 50%. In one embodiment, the FF is at least about 60%. In one embodiment, the FF is at least about 70%. In one embodiment, the FF is at least about 80%. In one embodiment, the FF is between about 10% and 90%. In one embodiment, the FF is between about 10% and 80%. In one embodiment, the FF is between about 20% and 80%. In one embodiment, the FF is between about 30% and 80%. In one embodiment, the FF is between about 40% and 80%. In one embodiment, the FF is between about 50% and 80%. In one embodiment, the FF is between about 55% and 75%. In one embodiment, the device having a high FF comprises the non-fullerene acceptor compound BT-IC. In one embodiment, the device having a high FF comprises the non-fullerene acceptor compound BT-CIC. In one embodiment, the device having a high FF comprises the non-fullerene acceptor compound BT-CIC-IC.

In one embodiment, an OPV device comprising a non-fullerene acceptor of formula (1) has a high short circuit current ($J_{SC}$). In one embodiment, the $J_{SC}$ is between about 5 mA/cm$^2$ and about 70 mA/cm$^2$. In one embodiment, the $J_{SC}$ is between about 5 mA/cm$^2$ and about 60 mA/cm$^2$. In one embodiment, the $J_{SC}$ is between about 5 mA/cm$^2$ and about 50 mA/cm$^2$. In one embodiment, the $J_{SC}$ is between about 5 mA/cm$^2$ and about 40 mA/cm$^2$. In one embodiment, the $J_{SC}$ is between about 5 mA/cm$^2$ and about 30 mA/cm$^2$. In one embodiment, the $J_{SC}$ is between about 10 mA/cm$^2$ and about 30 mA/cm$^2$. In one embodiment, the $J_{SC}$ is between about 15 mA/cm$^2$ and about 30 mA/cm$^2$. In one embodiment, the $J_{SC}$ is between about 15 mA/cm$^2$ and about 25 mA/cm$^2$. In one embodiment, the device having a high $J_{SC}$ comprises the non-fullerene acceptor compound BT-IC. In one embodiment, the device having a high $J_{SC}$ comprises the non-fullerene acceptor compound BT-CIC. In one embodiment, the device having a high $J_{SC}$ comprises the non-fullerene acceptor compound BT-CIC-IC.

In one embodiment, an OPV device comprising a non-fullerene acceptor of formula (1) has a high external quantum efficiency (EQE). In one embodiment, the EQE is between about 10% and 90%. In one embodiment, the EQE is between about 10% and 80%. In one embodiment, the EQE is between about 20% and 80%. In one embodiment, the EQE is between about 30% and 80%. In one embodiment, the EQE is between about 40% and 80%. In one embodiment, the EQE is between about 50% and 80%. In one embodiment, the EQE is between about 60% and 80%. In one embodiment, the EQE is between about 65% and 80%. In one embodiment, the device having a high EQE comprises the non-fullerene acceptor compound BT-IC. In one embodiment, the device having a high EQE comprises the non-fullerene acceptor compound BT-CIC. In one embodiment, the device having a high EQE comprises the non-fullerene acceptor compound BT-CIC-IC.

Experimental Examples

The invention is now described with reference to the following Examples. These Examples are provided for the purpose of illustration only, and the invention is not limited to these Examples, but rather encompasses all variations that are evident as a result of the teachings provided herein.

Materials and Methods

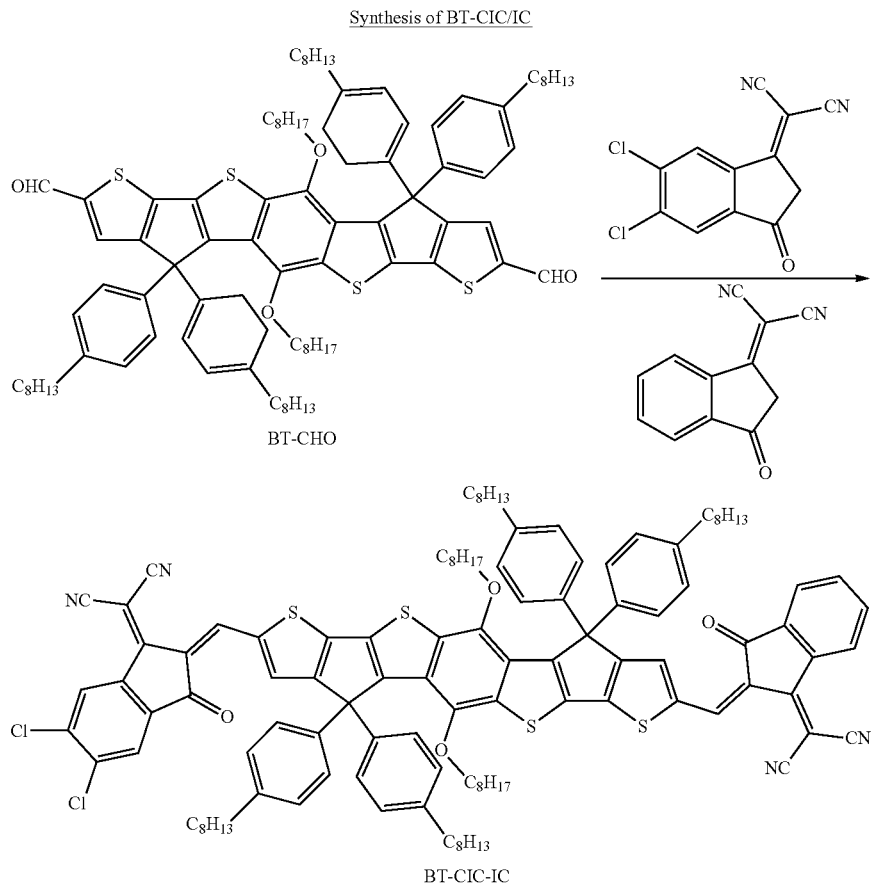

Synthesis of BT-CIC/IC

BT-CHO

BT-CIC-IC 3-(dicyanomethylidene)-5,6-dichloro-indan-1-one (79 mg, 0.3 mmol) and 3-(dicyanomethylidene)-indan-1-one (58 mg, 0.3 mmol) were added into the mixture of compound BT-CHO (400 mg, 0.3 mmol) in anhydrous chloroform with pyridine (1 mL), the reaction was deoxygenated with nitrogen for 30 min and then refluxed for 10 h. After cooling to room temperature, the solution was poured into methanol and the precipitate was filtered off. The filtered precipitate was extracted with DCM and washed with water. The crude product was purified by silica gel column using a mixture of hexane/DCM (3:2) as the eluent to give a purple solid (55%). $^1$H NMR (600 MHz, CDCl$_3$, δ): 8.80 (br, 4H), 8.74 (s, 2H), 8.67 (d, J=6.0 Hz, 2H), 7.90 (s, 2H), 7.89 (d, J=6.0 Hz, 2H), 7.73 (m, 4H), 7.50 (d, J=6.0 Hz, 2H), 7.49 (s, 2H), 7.30 (d, J=6.0 Hz, 8H), 7.08 (d, J=6.0 Hz, 8H), 3.49 (m, 4H), 2.56 (t, J=6.0 Hz, 8H), 1.59-1.54 (m, 8H), 1.35-1.29 (m, 42H), 0.96 (t, J=6.0 Hz, 6H), 0.86 (m, 18H). $^{13}$C NMR (125 MHz, CDCl$_3$, δ): 188.5, 186.2, 164.8, 164.5, 160.3, 158.1, 158.0, 157.0, 153.6, 146.4, 142.3, 142.2, 140.8, 139.9, 139.2, 139.0, 138.8, 138.6, 138.4, 138.2, 136.8, 136.0, 135.9, 135.8, 135.6, 135.1, 134.3, 128.4, 128.3, 126.9, 125.1, 125.0, 121.4, 114.7, 114.6, 39.3, 35.5, 31.7, 31.2, 29.5, 29.2, 28.7, 23.3, 22.7, 22.6, 14.2, 14.1, 10.8.

Resonant Soft X-Ray Diffraction

Resonant soft x-ray diffraction of the thin films was performed at beamline 11.0.1.2 at the Advanced Light Source (ALS), Lawrence Berkeley National Lab (LBNL) with photon energy of 286.2 eV. Thin films were prepared by use of the same method as for solar cell devices. The organic film was then transferred onto a Si$_3$N$_4$ substrate and the experiment was done in the transition mode.

Results and Discussion

The present invention relates to the development of a molecular design strategy to further reduce energy loss in OPV devices comprising a non-fullerene acceptor. Currently, all acceptor-donor-acceptor (a-d-a)-type non-fullerene acceptors have symmetric electron-withdrawing end groups that possess a nearly zero dipole moment. However, asymmetric electron withdrawing end groups in a-d-a molecules can provide freedom to tune the dipole moment and further reduce exciton bonding energy, thus decreasing energy loss. A series of non-fullerene acceptors with asymmetric molecular structures is disclosed herein. The initial results for these molecules with polymer donors showed efficiencies over 10% with a small energy loss of ~0.5 eV.

Figure 3:
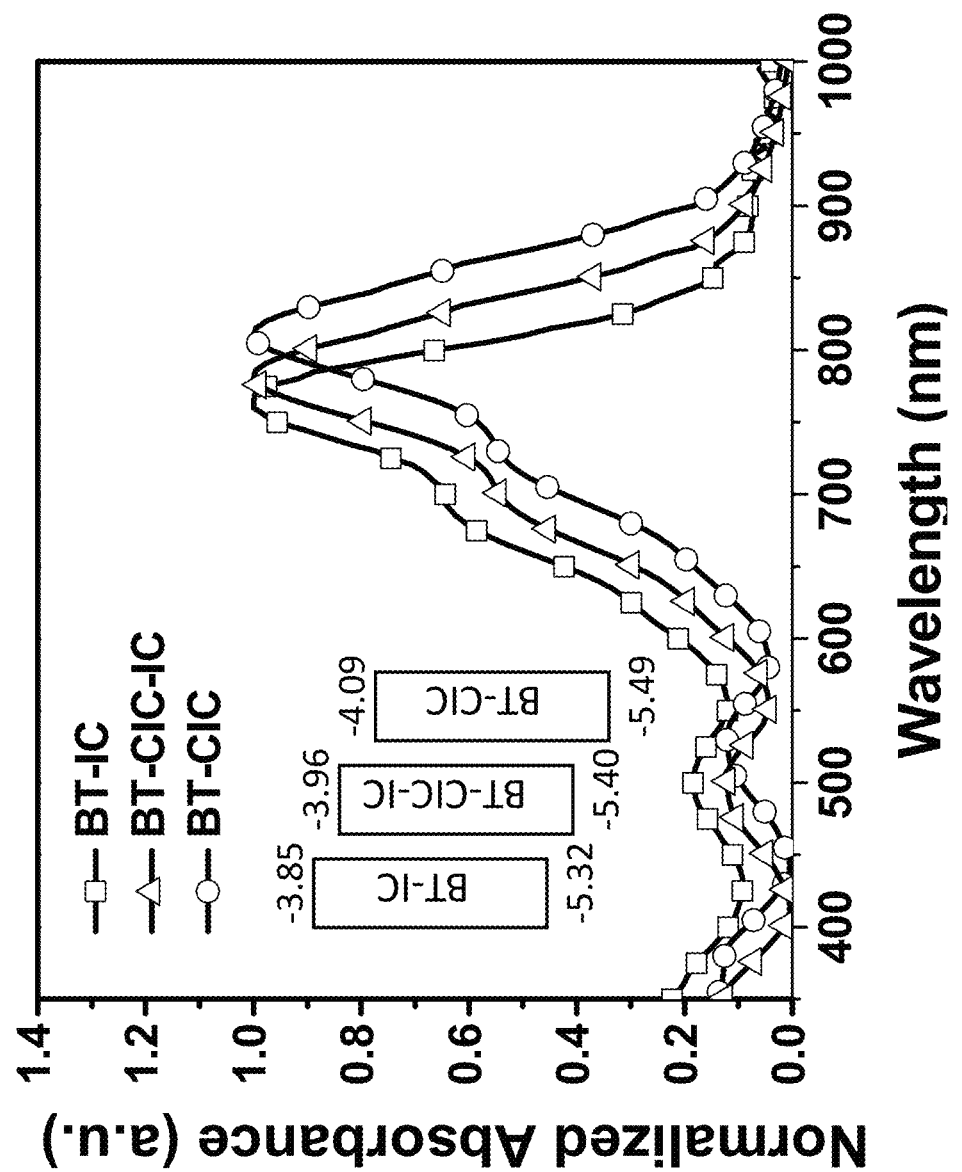
FIG. 3 depicts the UV-Vis absorption spectra of BT-IC, BT-CIC and BT-CIC-IC in chloroform solution. Inset: Energy diagram of BT-IC, BT-CIC and BT-CIC-IC relative to vacuum obtained from cyclic voltammetry.

UV-Vis absorption spectra of BT-IC, BT-CIC, and BT-CIC-IC in chloroform solution are shown in FIG. 3. BT-CIC-IC absorbs between a, =600 nm and 850 nm while being transparent in the visible, with an optical bandgap of 1.44 eV as determined from the absorption onset at a, =850 nm. Importantly, BT-CIC exhibits a bathochromic shift of ~20 nm compared to BT-IC, which suggests increased internal charge transfer. Cyclic voltammetry was used to obtain the highest occupied (HOMO) and the lowest unoccupied molecular orbital (LUMO) energies ($E_{HOMO}$ and $E_{LUMO}$, respectively) of −5.32 (±0.03) and −3.85 (±0.02) eV, respectively, for BT-IC; −5.49 (±0.02) and −4.09 (±0.02) eV, respectively, for BT-CIC; and −5.40 (±0.02) and −3.96 (±0.03) eV, respectively, for BT-CIC-IC. Both BT-CIC and BT-CIC-IC show the lower HOMO-LUMO energy gap (1.40 eV for BT-CIC and 1.44 eV for BT-CIC-IC) than BT-IC (1.47 eV), which is consistent with experimental result from the optical measurement. BT-CIC-IC exhibits both lower HOMO and LUMO energies compared with BT-IC due to the electron-withdrawing ability of the Cl atoms in the former molecule. The lower $E_{LUMO}$ leads to increased chemical stability and improved electron injection efficiency as the Schottky barrier with the cathode contact is decreased.

Figure 4:
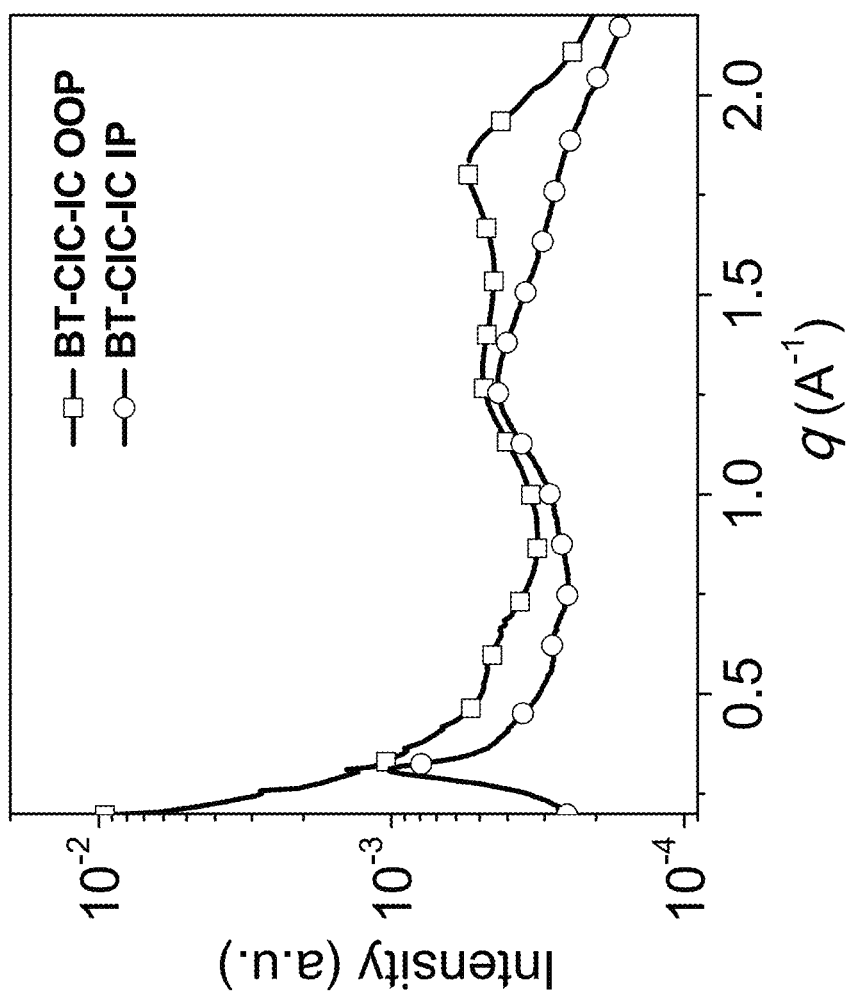
FIG. 4 depicts the n-plane (black line) and out-of-plane (red line) x-ray scattering patterns extracted from 2D grazing incidence x-ray diffraction (GIXD) images of BT-CIC/IC. Q is the scattering vector.

The morphology of BT-CIC-IC was characterized by glancing incidence x-ray diffraction (FIG. 4). The (100) diffraction peak of BT-CIC-IC is located at 0.38 Å$^{-1}$ with a crystal correlation length of =4.2±0.1 nm. The (010) diffraction peaks of BT-CIC-IC, particularly in the out-of-plane direction, are located at 1.3 and 1.8 Å$^{-1}$, which indicates that there are two different types of π-stacking in the BT-CIC-IC film as result of the dipole nature of BT-CIC-IC.

Figure 5:
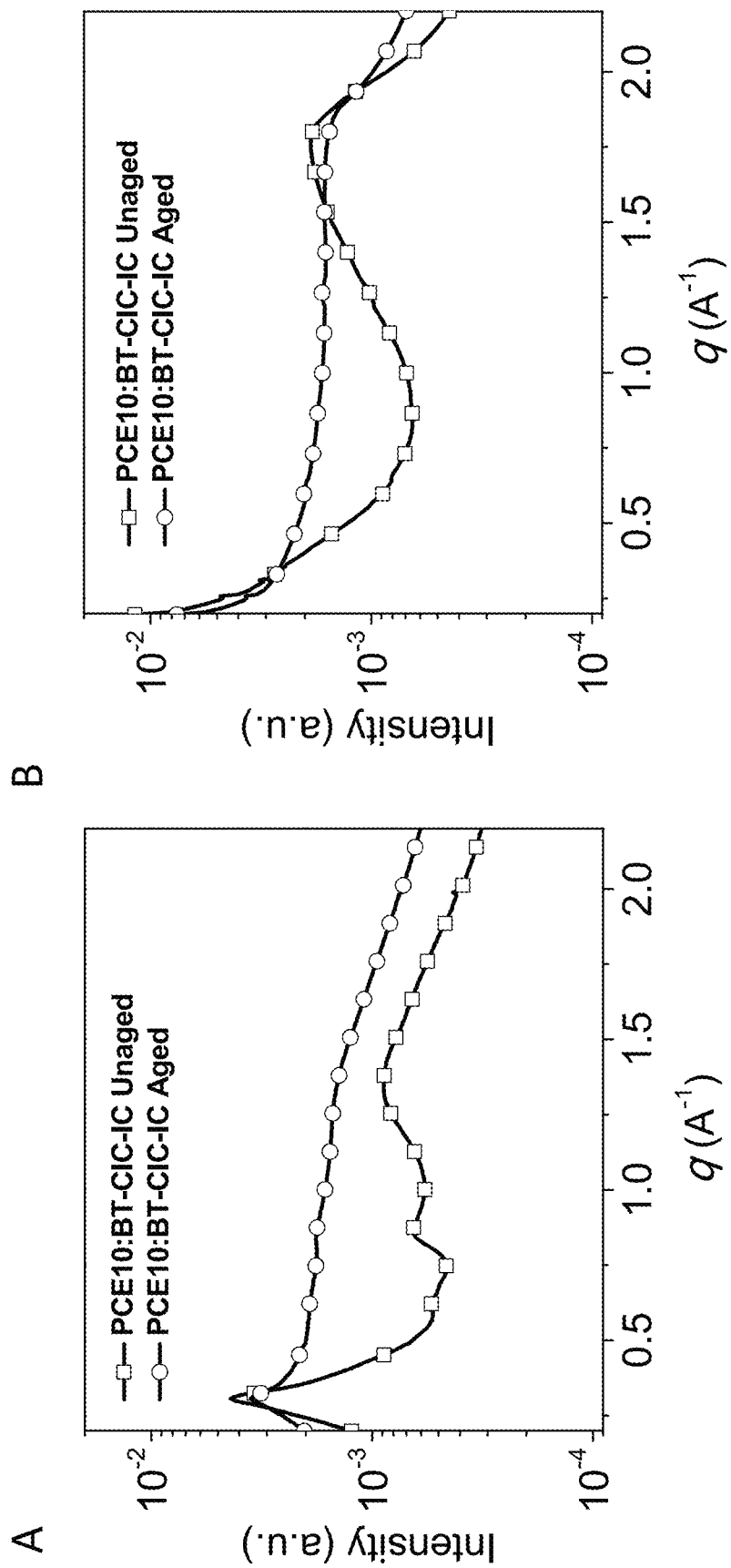
FIG. 5, comprising

FIGS. 5A-B show the morphological stability of a PCE-10:BT-CIC-IC blend film before and after aging wherein the film was continuously exposed to 1 kW/m$^2$ (1 sun), simulated AM1.5G illumination from a Xe-arc lamp for 100 h. Aging causes a significant effect on the PCE-10:BT-CIC-IC blend film, suggesting that the as-cast morphology is unstable. The (100) diffraction peak of PCE-10:BT-CIC-IC after 100 hrs of aging shows an increase in intensity at 0.38, 0.90, and 1.3 Å$^{-1}$, which is due to the high degree of crystallinity of BT-CIC-IC. In addition, a strong crystalline feature at ~1.8 Å$^{-1}$ is observed in the out-of-plane direction (FIG. 5B), which is dominated by the contribution from BT-CIC-IC since the (010) peak is located at 1.8 Å$^{-1}$.

Figure 6:
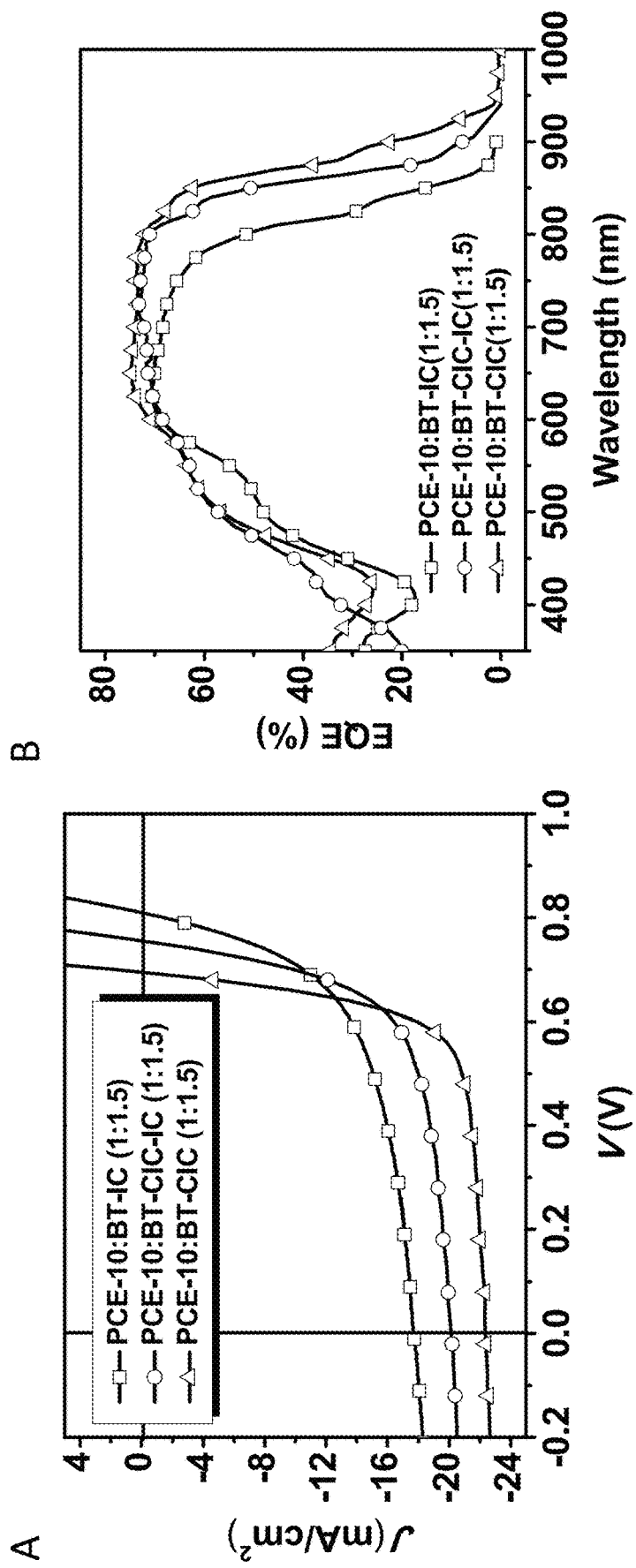
FIG. 6, comprising

The OPVs had device structures of: indium tin oxide (ITO)/ZnO (25 nm)/PCE-10 mixed with BT-IC, BT-CIC, or BT-CIC-IC (130 nm)/MoO$_3$ (15 nm)/Ag (100 nm). The current-density-voltage (J-V) characteristics are plotted in FIG. 6A, with the detailed device parameters summarized in Table 1. The devices for PCE-10:BT-IC, BT-CIC or BT-CIC-IC were spin-coated from 9:1 chlorobenzene:chloroform solution mixed with a 1:1.5 donor:acceptor (D:A) weight ratio. The highest PCE=11.2±0.4% was achieved in the BT-CIC based device, with $V_{oc}$=0.70±0.01 V, $J_{sc}$=22.5±0.6 mA cm-2, and FF=0.71±0.02 under a simulated AM1.5G, one sun intensity solar spectrum. In contrast, the BT-CIC-IC-based OPV exhibited PCE=10.6±0.3% with $V_{oc}$=0.76±0.01 V, $J_{sc}$=20.8±0.4 mA cm$^{-2}$ and FF=0.66±0.01. For the PCE-10:BT-IC device, PCE=8.3±0.2% with $V_{oc}$=0.81±0.01 V, $J_{sc}$=17.5±0.4 mA cm$^{-2}$ and FF=0.60±0.02. BT-CIC-IC and BT-CIC exhibit lower LUMO energies compared with BT-IC, which leads to decreased $V_{oc}$. The EQE vs. wavelength spectrum is shown in FIG. 6B. The significant improvement in $J_{sc}$ for the BT-CIC and BT-CIC-IC OPV are attributed to their red-shifted absorption caused by the electron-withdrawing ability of the Cl atoms in these two molecules, that provide solar spectral response into the NIR.

TABLE 1

Operating characteristics of OPVs under simulated of AM 1.5 G, 100 mW cm$^{-2}$, illumination.

| Acceptor[a] | $J_{sc}$[b] [mA/cm$^2$] | $V_{oc}$ [V] | FF [%] | PCE[c] [%] |
|---|---|---|---|---|
| BT-IC | 17.5 ± 0.4 (16.7) | 0.81 ± 0.01 | 59.6 ± 1.5 | 8.3 ± 0.2 |
| BT-CIC | 22.5 ± 0.6 (21.3) | 0.70 ± 0.01 | 71.0 ± 1.9 | 11.2 ± 0.4 |
| BT-CIC-IC | 20.8 ± 0.4 (20.5) | 0.76 ± 0.01 | 65.6 ± 1.0 | 10.6 ± 0.3 |

[a]All blends are donor:acceptor 1:1.5. The donor is PCE-10.
[b]The values in parentheses are calculated from the integral of the EQE spectrum.
[c]The average value is based on measurement of 8 devices.

Figure 7:
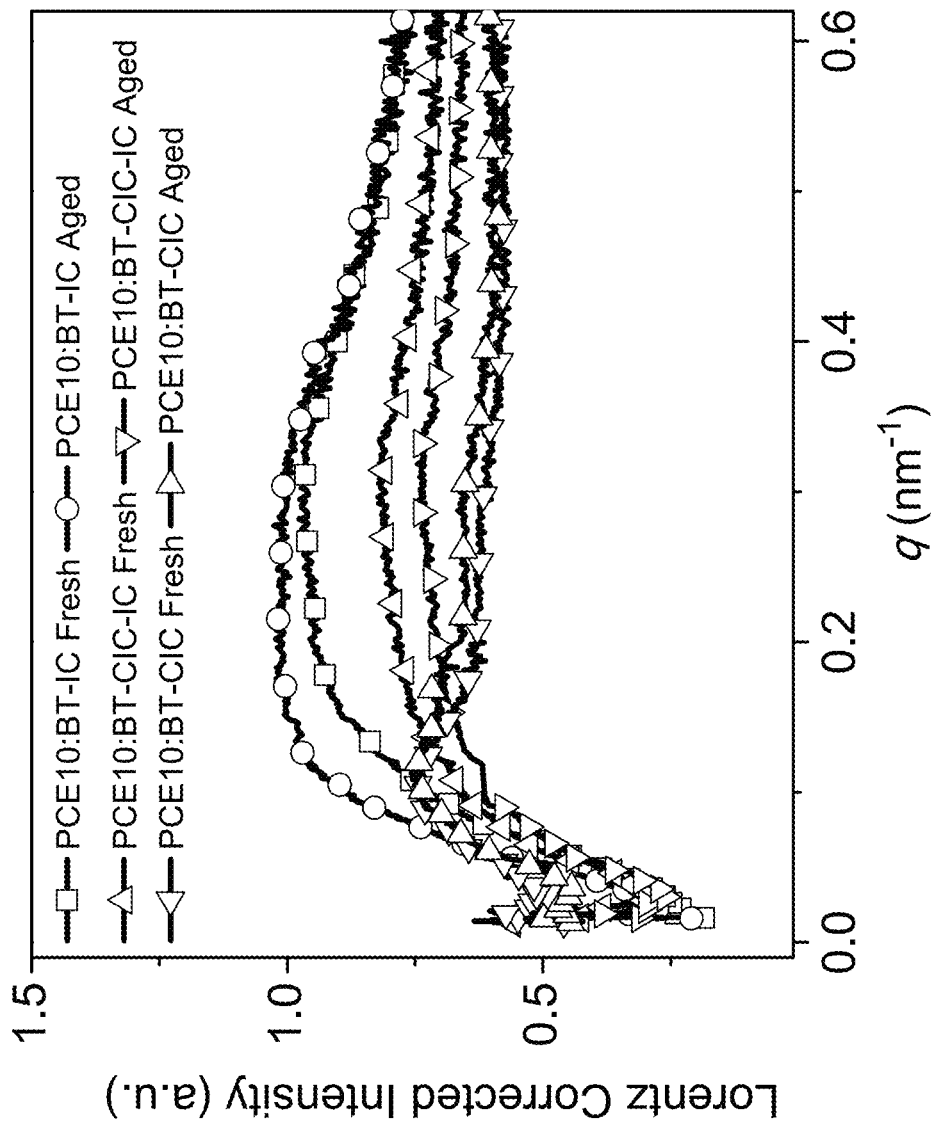
FIG. 7 depicts resonant soft X-ray diffraction studies of fresh and aged PCE-10:BT-IC, PCE-10:BT-CIC, and PCE-10:BT-CIC-IC blends.

Phase separation of the donor/acceptor blends with aging was studied by resonant soft X-ray diffraction as shown in FIG. 7, wherein "fresh" refers to a sample that was just prepared and "aged" refers to a sample that was photoaged under continuous illumination from a Xe arc lamp solar simulator at an intensity of 1 kW/m$^2$. The results of this study indicate that the PCE-10:BT-IC blend shows a bimodal size distribution (i.e. can be fitted with two lognormal peaks), while the PCE-10:BT-CIC and PCE-10:BT-CIC-IC blends exhibit single lognormal distributions. In addition, a comparison of the phase purity of these three blended films, as represented by the ISI (FIG. 8), shows some differences. The purity of the PCE10:BT-IC blend is slightly increased after aging, while the PCE10:BT-CIC-IC blend is slightly decreased after aging. In contrast, the phase purity of the PCE10:BT-CIC blend is almost unchanged, which indicates the morphological stability of the PCE10:BT-CIC blend.

Figure 9:
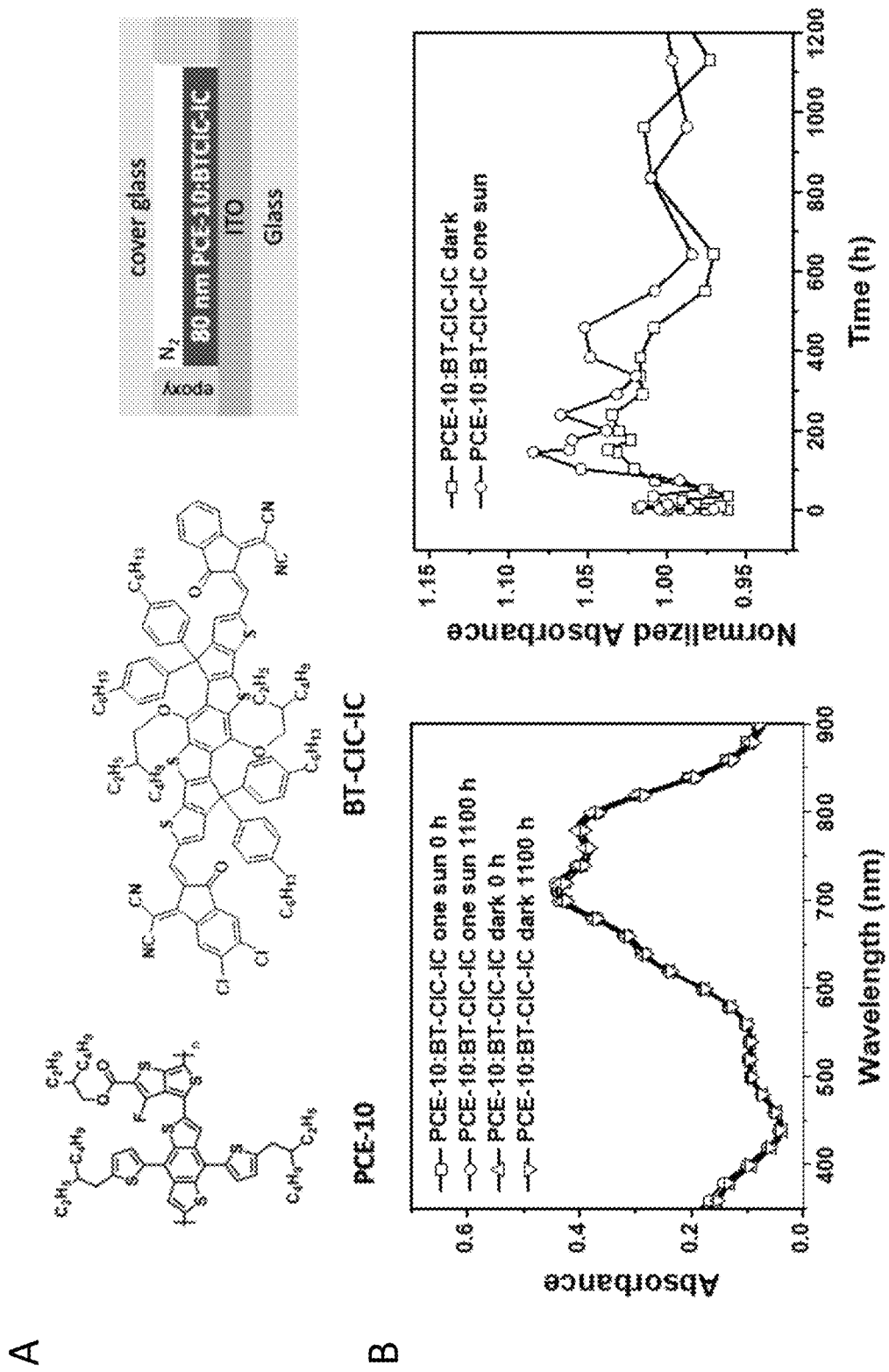
FIG. 9, comprising
Figure 10:
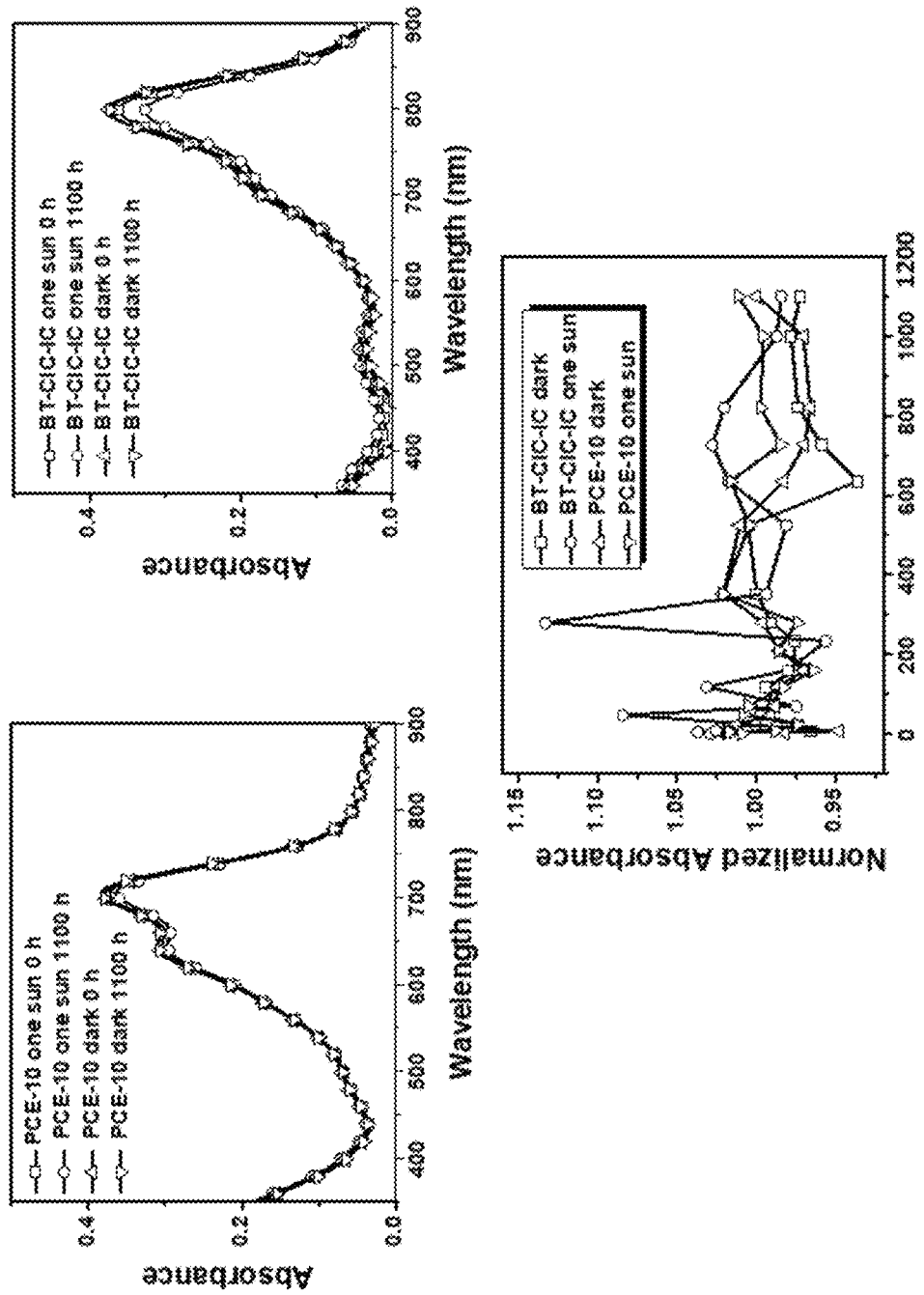
FIG. 10 depicts photostability studies of PCE-10 donor and BT-CIC-IC acceptor samples under continuous illumination from a Xe arc lamp solar simulator at an intensity of 1 kW/m$^2$.

The photostability of blended films comprising a PCE-10 donor and BT-CIC-IC acceptor was studied (FIG. 9A-B). When films stored in the air under darkness were compared to those aged under continuous illumination from a Xe arc lamp solar simulator at an intensity of 1 kW/m$^2$, the films exposed to both sets of conditions show an identical absorption spectrum, which indicates no apparent degradation was observed in these blended films. Similarly, studies of the photostability of an unblended PCE-10 donor and unblended BT-CIC-IC acceptor show no obvious photobleaching under continuous illumination from a Xe arc lamp solar simulator at an intensity of 1 kW/m$^2$ (FIG. 10).

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A compound of formula (1) or a stereoisomer thereof:

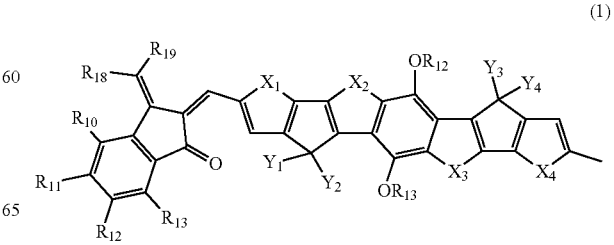

(1)

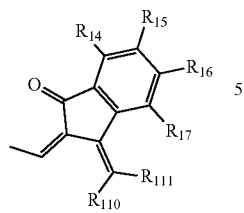

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$-alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof;

wherein $R_{11}$ and $R_{12}$ are the same; and $R_{15}$ and $R_{16}$ are the same;

$R_{18}$, $R_{19}$, $R_{110}$, and $R_{111}$ are each independently an electron withdrawing group selected from the group consisting of: halogen, $C(=O)R_{116}$, $SO_3R_{117}$, cyano, nitro, $C(R_{118})_3$, and combinations thereof;

$R_{114}$-$R_{117}$ are each independently selected from the group consisting of hydrogen and $C_1$-$C_{20}$ alkyl;

$R_{118}$ is a halogen selected from the group consisting of F, Cl, Br, and I;

$R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl;

$X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof;

wherein the compound of formula (1) is asymmetric.

2. The compound of claim 1, wherein each of $X_1$-$X_4$ are S.

3. The compound of claim 1, wherein $R_{10}$-$R_{13}$, $R_{14}$, and $R_{17}$ are each hydrogen; and $R_{15}$ and $R_{16}$ are each independently a halogen selected from the group consisting of: F, Cl, Br, and I.

4. The compound of claim 3, wherein $R_{15}$ and $R_{16}$ are each Cl.

5. The compound of claim 1, wherein $R_{18}$, $R_{19}$, $R_{110}$, and $R_{111}$ are each cyano.

6. The compound of claim 1, wherein $Y_1$-$Y_4$ are each independently selected from the group consisting of:

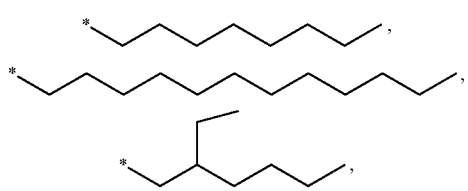

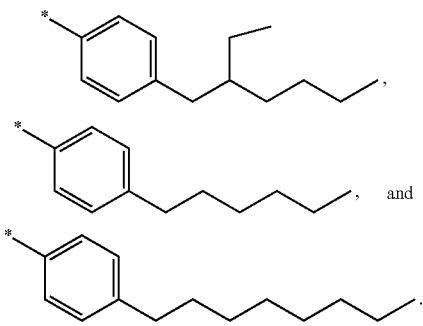

7. The compound of claim 1, wherein $Y_1$-$Y_4$ are each

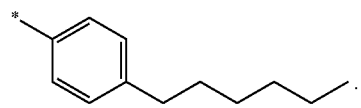 [SMILES: *c1ccc(CCCCCC)cc1]

8. The compound of claim 1, wherein $R_{112}$ and $R_{113}$ are each independently selected from the group consisting of:

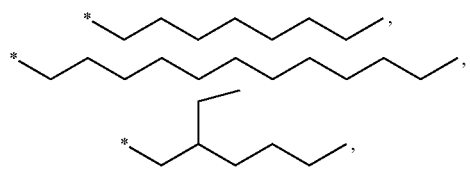

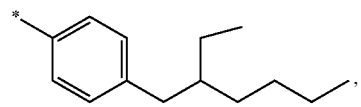

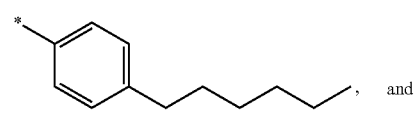

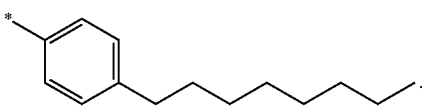

9. The compound of claim 1, wherein $R_{112}$ and $R_{113}$ are each independently

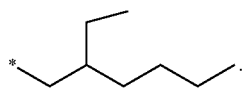

10. The compound of claim 1, wherein the compound of formula (1) is selected from the group consisting of:
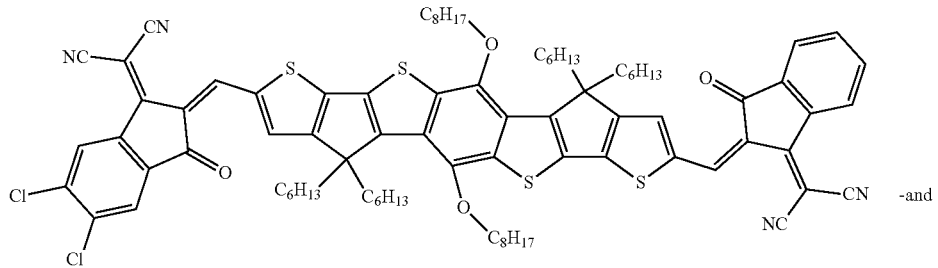 -and
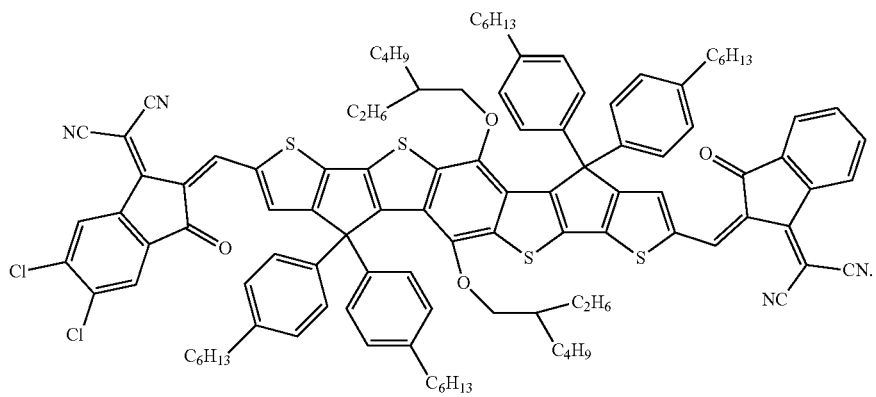
11. An organic photovoltaic device comprising:
an anode,
a cathode, and
an active layer between the anode and the cathode, wherein the active layer comprises a compound of formula (1) or a stereoisomer thereof:
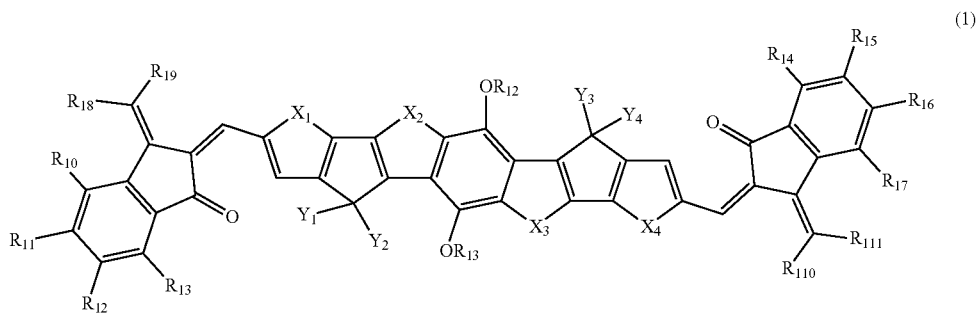
(1)

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$ alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof;

wherein $R_{11}$ and $R_{12}$ are the same; and $R_{15}$ and $R_{16}$ are the same;

$R_{18}$, $R_{19}$, $R_{110}$, and $R_{111}$ are each independently an electron withdrawing group selected from the group consisting of: halogen, $C(=O)R_{116}$, $SO_3R_{117}$, cyano, nitro, $C(R_{118})_3$, and combinations thereof;

$R_{114}$-$R_{117}$ are each independently selected from the group consisting of hydrogen and $C_1$-$C_{20}$ alkyl;

$R_{118}$ is a halogen selected from the group consisting of F, Cl, Br, and I;

$R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl;

$X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof;

wherein the compound of formula (1) is asymmetric.

12. The organic photovoltaic device of claim 11, wherein the active layer further comprises a polymer selected from the group consisting of:

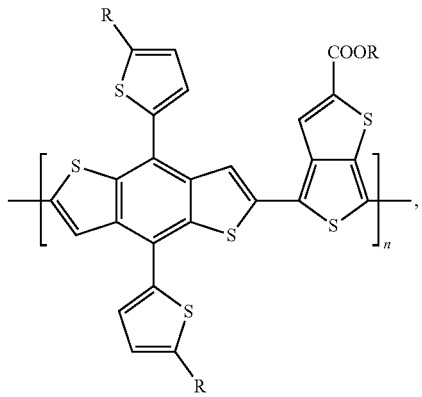

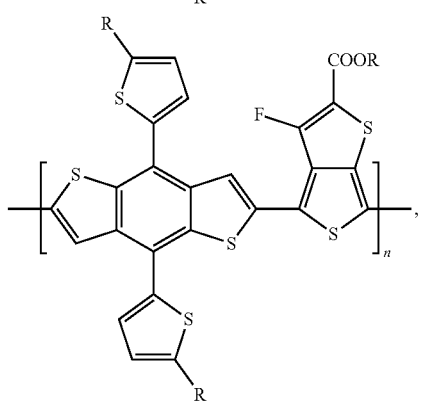

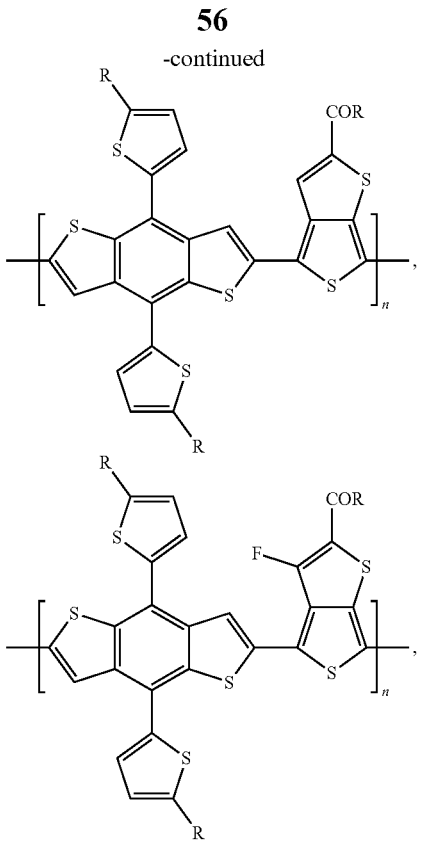

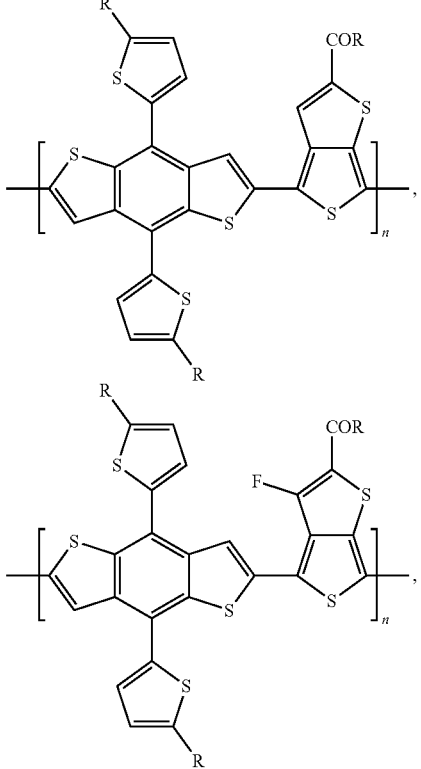

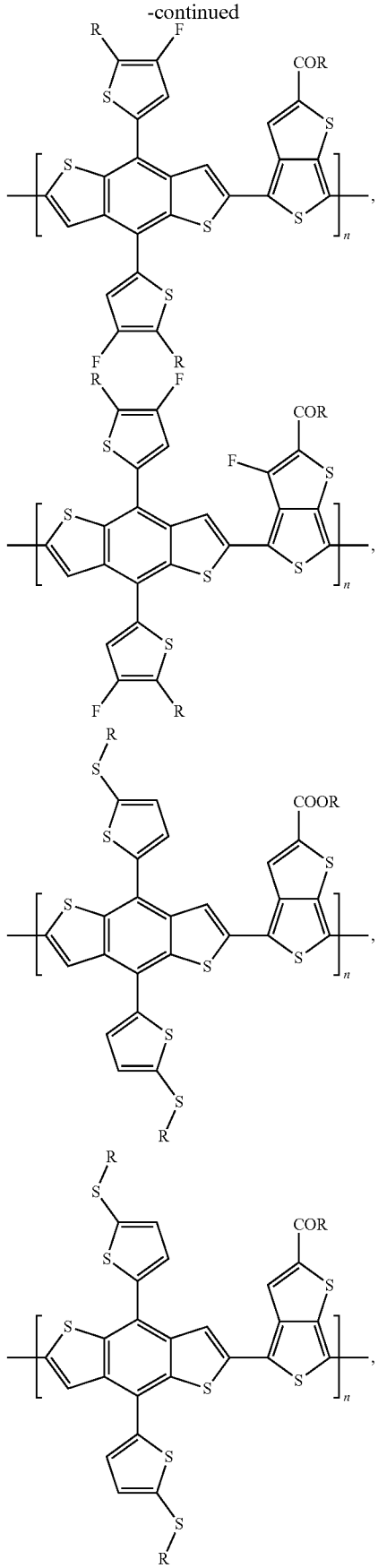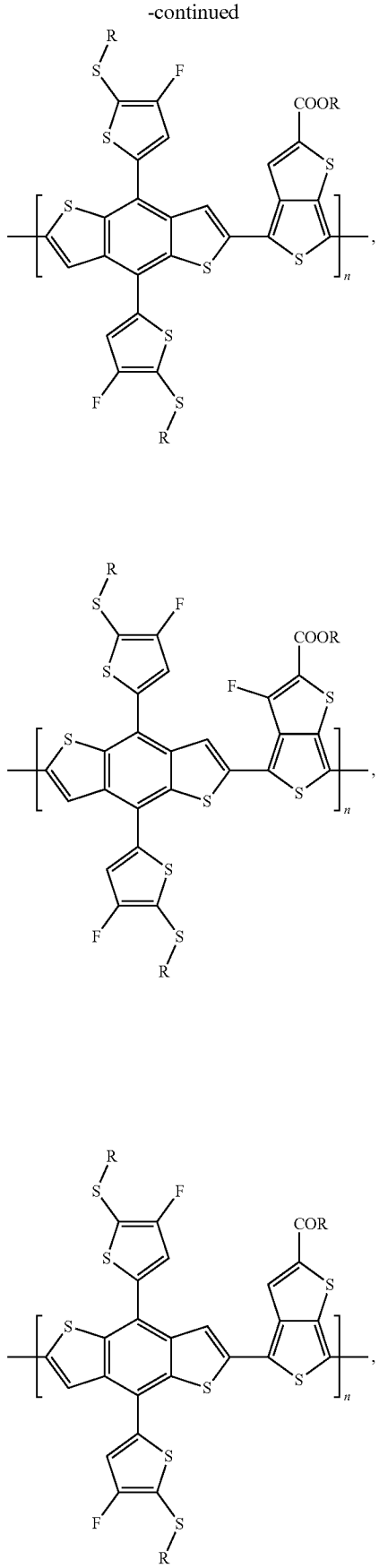

-continued

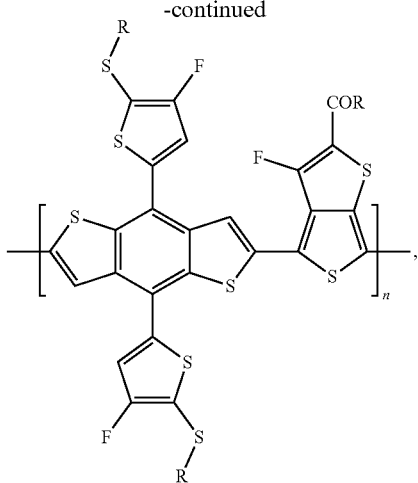

and derivatives thereof;
wherein each R is independently a $C_1$-$C_{20}$ alkyl; and n is the degree of polymerization.

13. The organic photovoltaic device of claim 12, wherein the polymer comprises

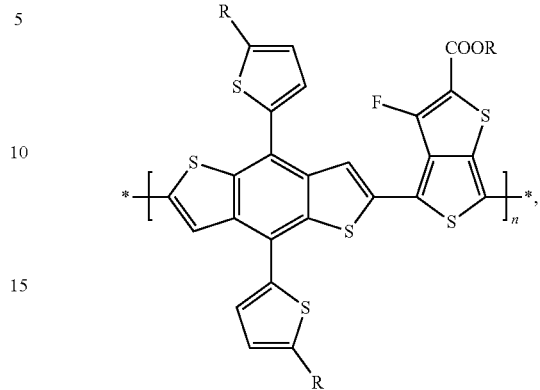

wherein each R is independently a $C_1$-$C_{20}$ alkyl; and n is the degree of polymerization.

14. The organic photovoltaic device of claim 13, wherein each R represents 2-ethylhexyl.

15. The organic photovoltaic device of claim 11, wherein in the acceptor represented by formula (1) is selected from the group consisting of:

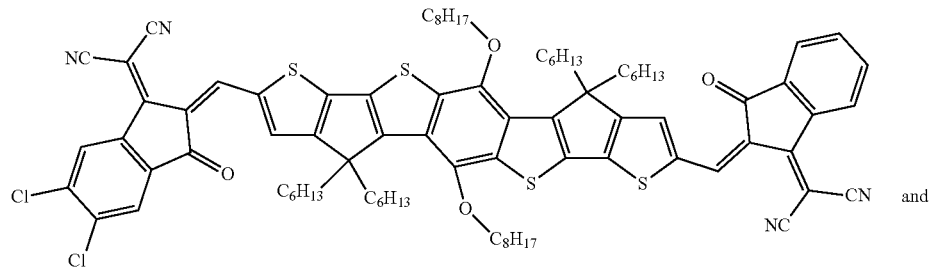 and

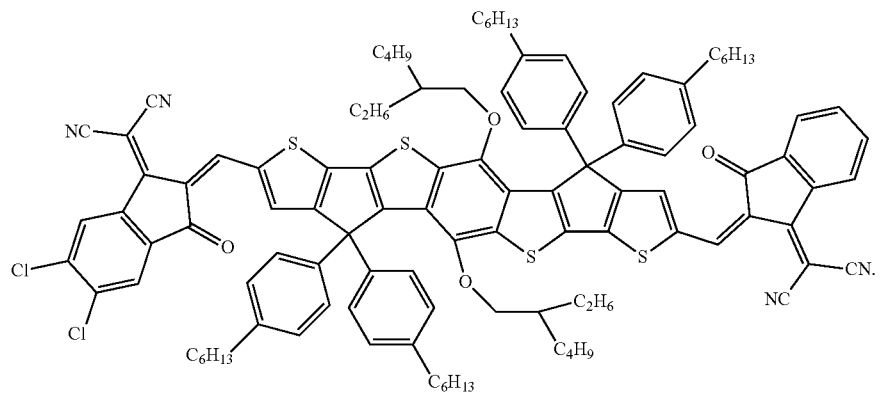

16. The organic photovoltaic device of claim 11, wherein the device has an open circuit voltage of between about 0.5 V and 1 V; or wherein the device has a fill factor between about 55% and 75%.

17. The organic photovoltaic device of claim 11, wherein the device has a short circuit current of between about 15 mA/cm² and 25 mA/cm².

18. The organic photovoltaic device of claim 11, wherein the device has an external quantum efficiency of between about 65% and 80%.

19. A formulation comprising a compound of formula (1) or a stereoisomer thereof:

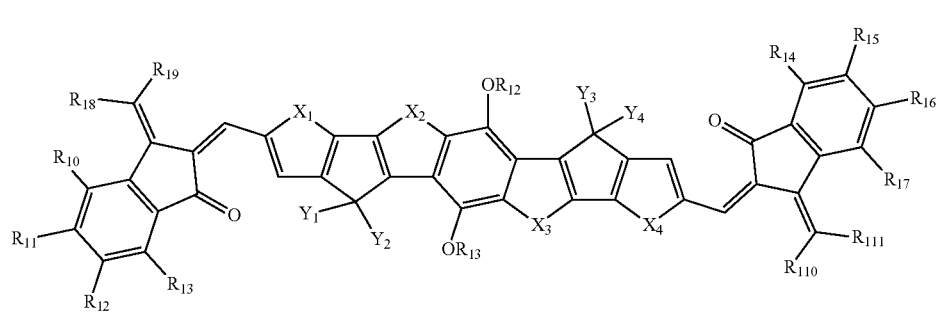

(1)

wherein $R_{10}$-$R_{17}$ are each independently selected from the group consisting of hydrogen, deuterium, $C_1$-$C_6$ alkyl, halogen, $CO_2R_{114}$, $OR_{115}$, $C_3$-$C_6$ cycloalkyl, $C_2$-$C_4$ alkynyl, $C_2$-$C_4$ alkenyl, alkoxy, alkylthio, aryl, $C_1$-$C_6$ heteroalkyl, $C_3$-$C_6$ heterocycyl, $C_3$-$C_6$ heteroaryl, amido, amino, cyano, and combinations thereof;

wherein $R_{11}$ and $R_{12}$ are the same; and $R_{15}$ and $R_{16}$ are the same;

$R_{18}$, $R_{19}$, $R_{110}$, and $R_{111}$ are each independently an electron withdrawing group selected from the group consisting of: halogen, $C(=O)R_{116}$, $SO_3R_{117}$, cyano, nitro, $C(R_{118})_3$, and combinations thereof;

$R_{114}$-$R_{117}$ are each independently selected from the group consisting of hydrogen and $C_1$-$C_{20}$ alkyl;

$R_{118}$ is a halogen selected from the group consisting of F, Cl, Br, and I;

$R_{112}$, $R_{113}$, and $Y_1$-$Y_4$ are each independently selected from the group consisting of substituted or unsubstituted $C_1$-$C_{20}$ alkyl, substituted or unsubstituted $C_6$-$C_{10}$ aryl, and substituted or unsubstituted $C_6$-$C_{10}$ heteroaryl;

$X_1$-$X_4$ are each independently selected from the group consisting of S, O, NR, CRR', SiRR', and Se; and R and R' are each independently selected from the group consisting of hydrogen, $C_1$-$C_{20}$ alkyl, $C_6$-$C_{10}$ aryl, $C_6$-$C_{10}$ heteroaryl, and combinations thereof;

wherein the compound of formula (1) is asymmetric.

* * * * *